US010036736B2

(12) United States Patent
Nichols et al.

(10) Patent No.: US 10,036,736 B2
(45) Date of Patent: *Jul. 31, 2018

(54) LIQUID SAMPLING VALVE

(71) Applicant: IDEX Health & Science LLC, Rohnert Park, CA (US)

(72) Inventors: Jon Nichols, Forrestville, CA (US); Michael Keller, Napa, CA (US); Audrey Schrock, Santa Rosa, CA (US); Carl Sims, Santa Rosa, CA (US); Carl Servin, Novato, CA (US)

(73) Assignee: IDEX Health & Science LLC, Rohnert Park, CA (US)

( * ) Notice: Subject to any disclaimer, the term of this patent is extended or adjusted under 35 U.S.C. 154(b) by 395 days.

This patent is subject to a terminal disclaimer.

(21) Appl. No.: 14/714,834

(22) Filed: May 18, 2015

(65) Prior Publication Data

US 2015/0247827 A1 Sep. 3, 2015

Related U.S. Application Data

(63) Continuation of application No. 14/370,084, filed as application No. PCT/US2013/050909 on Jul. 17, 2013, now Pat. No. 9,032,819.

(Continued)

(51) Int. Cl.
*G01N 30/20* (2006.01)
*F16K 11/074* (2006.01)
(Continued)

(52) U.S. Cl.
CPC .......... *G01N 30/20* (2013.01); *F16K 11/0743* (2013.01); *F16K 11/0853* (2013.01);
(Continued)

(58) Field of Classification Search
CPC .......... G01N 30/20; G01N 1/14; G01N 30/40
(Continued)

(56) References Cited

U.S. PATENT DOCUMENTS 3,116,642 A 1/1964 Wier
3,645,142 A 2/1972 Turpin
(Continued)

FOREIGN PATENT DOCUMENTS

FR 2862759 5/2005
GB 2290283 2/1995
(Continued)

OTHER PUBLICATIONS

Official Action issued in European Patent Application Serial No. 13819301.6 (dated Sep. 15, 2015).
(Continued)

*Primary Examiner* — John Fitzgerald
*Assistant Examiner* — Rodney T Frank
(74) *Attorney, Agent, or Firm* — Haugen Law Firm PLLP

(57) ABSTRACT

A liquid sampling system includes a liquid sampling valve for transferring a liquid sample from a primary stream to a secondary stream. The liquid sampling valve includes a rotor having a movable shuttle that is in selective fluid communication with the primary stream or the secondary stream. The rotor shuttle passes through a discharge station prior to completion of the valve cycle to discharge contaminants prior to re-exposure to the primary stream.

19 Claims, 17 Drawing Sheets

Related U.S. Application Data

(60) Provisional application No. 61/672,638, filed on Jul. 17, 2012.

(51) Int. Cl.

| | | |
|---|---|---|
| *G01N 35/10* | (2006.01) | |
| *G01N 1/20* | (2006.01) | |
| *F16K 11/085* | (2006.01) | |
| *G01N 30/40* | (2006.01) | |
| *G01N 30/46* | (2006.01) | |
| *G01N 1/14* | (2006.01) | |
| *G01N 30/02* | (2006.01) | |
| *G01N 30/72* | (2006.01) | |

(52) U.S. Cl.
CPC ............. *G01N 1/14* (2013.01); *G01N 1/2035* (2013.01); *G01N 30/40* (2013.01); *G01N 30/463* (2013.01); *G01N 30/7286* (2013.01); *G01N 35/1097* (2013.01); *G01N 30/7233* (2013.01); *G01N 2001/205* (2013.01); *G01N 2030/027* (2013.01); *G01N 2030/202* (2013.01)

(58) Field of Classification Search
USPC ........................................................ 73/863.86
See application file for complete search history.

(56) References Cited

U.S. PATENT DOCUMENTS

| | | |
|---|---|---|
| 6,012,488 A | 1/2000 | Nichols |
| 6,453,725 B1 | 9/2002 | Dahlgren |
| 6,890,489 B2 | 5/2005 | Nichols et al. |
| 7,503,203 B2 | 3/2009 | Gamache et al. |
| 7,575,723 B2 | 8/2009 | Nichols et al. |
| 8,112,182 B2 | 2/2012 | Tokuhisa et al. |

FOREIGN PATENT DOCUMENTS

| | | |
|---|---|---|
| JP | 63196861 | 8/1988 |
| JP | 1-113233 | 5/1991 |
| JP | 05273187 | 10/1993 |
| WO | 2010065138 | 6/2010 |

OTHER PUBLICATIONS

Supplemental European Search Report and Search Opinion issued in related European patent application serial No. 13819301.6.
English Translation of Office Action dated Mar. 3, 2015 in related Japanese patent application serial No. 2015-500685.

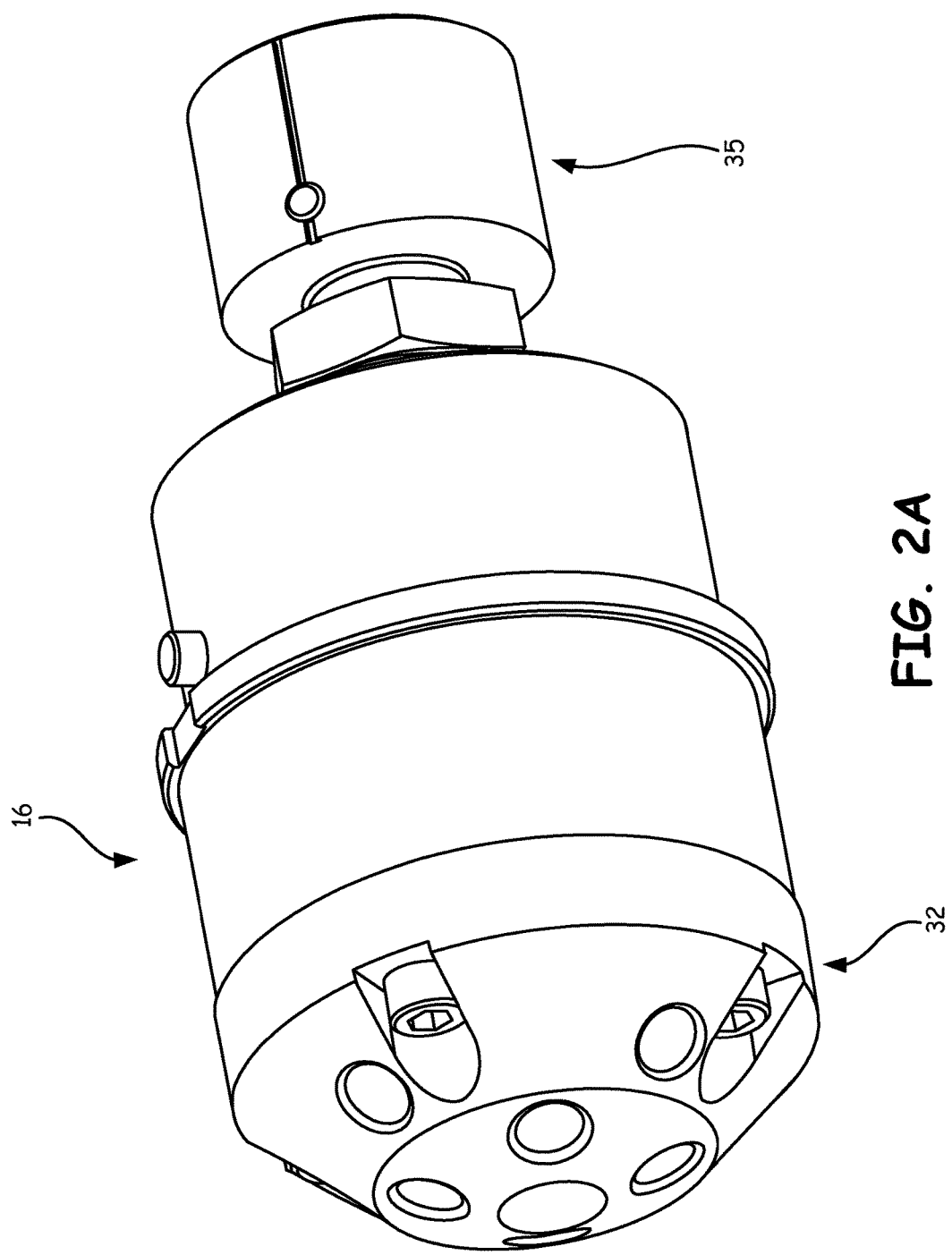

LIQUID SAMPLING VALVE

CROSS-REFERENCE TO RELATED APPLICATIONS

This application is a continuation of U.S. patent application Ser. No. 14/370,084, filed on Jul. 1, 2014 and entitled "Liquid Sampling Valve," which is a National Phase under 35 U.S.C. § 371 of International Application Serial No. PCT/US13/50909, filed on Jul. 17, 2013 and entitled "Liquid Sampling Valve," which itself claims priority to U.S. Provisional Patent Application Ser. No. 61/672,635, filed on Jul. 17, 2012 and entitled "Liquid Sampling Valve," the contents of which being incorporated herein in their entirety.

FIELD OF THE INVENTION

The present invention relates to liquid analysis systems, and more particularly to a liquid sampling valve for transferring a liquid sample from a primary stream to a secondary stream for analysis of the liquid sample in the secondary stream.

BACKGROUND OF THE INVENTION

A mixture of compounds, or analytes, can be separated by pumping the mixture through a separating device such as a chromatographic column using a process known as liquid chromatography, a variant of which is known as high performance liquid chromatography (HPLC). The separation of the sample is caused by analytes having different affinity for the chromatographic packing material within the column. The separated sample flows out of the chromatographic column continuously, but with the separated analytes emerging from the column at different times. The individual compounds comprising the analyte may then pass through various detection devices such as an ultraviolet light absorbance detector, a mass spectrometer, a fluorescence detector and the like to assist in determining the composition of the sample. The analytes may also be delivered to a receiver where each analyte might be stored in separate containers in a manner known as fraction collection. In some cases, a small amount of the column effluent may be directed to the inlet of another sample analysis device, such as a mass spectrometer to further analyze each individual analyte. The delivery of at least a portion of the column effluent to a further liquid analysis device is referred to as "second dimension" analysis, and is commonly employed in complex liquid analysis.

An example application for two dimensional liquid analyses is in the purification of a synthesized compound during the development of a new drug. Often, the products of the synthesis include the desired synthesized compound (with a known molecular weight), reactants and side products, all of which are analytes in the synthesis sample. In this example, a "first dimension" analysis carries out analytical or preparative scale separation, such as through an HPLC column, with a dedicated detection means such as a high flow rate refractive index detector or an ultraviolet light detector monitoring column effluent. A "second dimension" analysis may preferably utilize a second, separate flow path to capture a portion of the column effluent and direct the flow to a secondary analysis device, such as a mass spectrometer. Such combined instruments in a "two-dimensional" arrangement are becoming increasingly used to extend the understanding of the purity of compounds in a liquid scale.

For a second-dimension analysis device, such as a mass spectrometer, to function optimally, a controlled low mass rate of the eluent from the first dimension HPLC column containing the analyte should be delivered. Such mass or flow rates should be easily adjustable and closely controllable despite variations in the flow rate of the first dimension system. The flow rate should be reproducibly controlled, which facilitates second-dimension identification of the purity of an eluting peak of the desired synthesized compound to allow the collection of pure analyte in individual fractions. An experienced analyst may select a desired carrier fluid to transfer the analyte into the second-dimension detector, which second dimension carrier fluid may be different from the mobile phase used to perform the first-dimension preparative separation of the synthesized compound. Certain mobile phase fluids used to perform chromatographic separations may contain dissolved buffer salts which can cause fouling of a different second dimension analysis device such as a mass spectrometer, and certain organic components of the mobile phase can inhibit optimum ionization of the analytes which is required in a mass spectrometer. Proper selection of the carrier solvent reduces the effect on the mass spectrometer of the first-dimension analyte-mobile phase being transferred into the mass spectrometer. In addition, the analyte mass transfer rate into the mass spectrometer should be small, and generally should be a small fraction of the total analyte flow rate in the first dimension. A large mass rate to a mass spectrometer can result in a lingering or tailing signal that distorts the results of a mass spectrometer, and a large mass rate can change the dielectric properties of the system and cause a momentary loss of signal.

Some forms of secondary analysis devices may be better suited for receiving inlet flow at a rate that is significantly less than the flow rate typically passed through an HPLC separation column. Although modern mass spectrometers are designed with sample introduction systems wherein the flow rate of the inlet mobile phase can be as much as several milliliters per minute, such mass spectrometers utilize expensive high volume turbo molecular pumps and high volume roughing pumps to handle the large solvent loads. Reducing inlet flow rate can reduce or eliminate the need for such expensive equipment, and may also facilitate superior second dimension analysis. A desired approach, therefore, for second dimension liquid analysis is to supply only a representative portion of the first dimension flow to the second dimension analysis device. An example conventional mechanism for diverting a small fractional volume of analytes from a first dimension analysis system is shown in U.S. Pat. Nos. 6,890,489, and 7,575,723, assigned to the same assignee as in this application, and incorporated herein by reference.

Conventional "mass rate attenuators" or flow diversion apparatus typically do not permit sustained, continuous flow of a secondary analysis stream to a second dimension analysis device, which man be harmful to sensitive analysis equipment, such as in mass spectrometers. Moreover, conventional devices employ a "back and forth" switching mechanism transferring the analyte from the first dimension analysis to the secondary flow stream for the second dimension analysis, and then returning the carrier fluid flowing in the secondary flow stream back into the first dimension effluent. Returning the second dimension carrier liquid to the first dimension flow can contaminate the first dimension flow, which can frustrate efforts to obtain separated and purified analytes in the first dimension effluent.

It would therefore be of value to provide a device that is capable of separating out a very small closely controlled portion of a larger first dimension stream, and divert that portion along a secondary path without returning any portion of the flow from the second dimension to the first dimension flow stream.

SUMMARY OF THE INVENTION

By means of the present invention, measured samples from a first liquid stream may be transferred to a second liquid stream for analysis of the measured samples carried in the second liquid stream. A liquid sampling valve, which performs the sample transfer, is arranged to mitigate or eliminate contamination of the first liquid stream with carryback from the second liquid stream. The liquid sampling valve of the present invention a includes discharge function for flushing or rinsing out a leftover volume of the second liquid stream in a sample shuttle prior to returning the sample shuttle into fluid communication with the first liquid stream. The liquid sampling valve of the present invention is also arranged for 360° rotation about an axis of rotation, which enhances rotor actuator and valve component life span in comparison to conventional back and forth switching mechanisms.

A liquid sampling valve of the present invention includes a stator having a stator face, a primary stator passage extending along a primary path through the stator and opening to the stator face through a first primary port, an inlet secondary stator passage extending along a secondary path through the stator and opening to the stator face through a first port, an outlet secondary stator passage extending along the secondary path through the stator and opening to the stator face through a second port, an inlet discharge passage extending along a discharge path through the stator and opening to the stator face through a third port, and an outlet discharge passage extending along the discharge path through the stator and opening to the stator face through a fourth port. The liquid sampling valve further includes a rotor having a rotor face in fluid-tight contact with the stator face at an interface. The rotor face includes a shuttle that is configured to receive a liquid aliquot in fluid communication with the interface. The rotor is rotatable with respect to the stator about an axis of rotation to sequentially move the shuttle into a plurality of circumaxially spaced stations. A first station aligns the shuttle in fluid communication with the primary path at the first primary port, and a second station aligns the shuttle in fluid communication with the secondary path at the first and second ports. A third station aligns the shuttle in fluid communication with the discharge path at the third and fourth ports.

A liquid sampling system of the present invention includes the liquid sampling valve described above, as well as a primary stream supply delivering a primary stream to the primary stator passage along the primary path, and a secondary stream supply delivering a secondary stream to the inlet secondary stator passage along the secondary path. A liquid sampling system further includes a discharge stream supply driving a discharge from the liquid sampling valve.

A method for transferring a liquid sample from a primary stream to a secondary stream for analysis of the liquid sample in the secondary stream includes providing a liquid sampling valve having a stator with a stator face, a primary stator passage extending along a primary path through the stator and opening to the stator face. The stator further includes an inlet secondary stator passage extending along a secondary path through the stator and opening to the stator face, an outlet secondary stator passage extending along the secondary path through the stator and opening to the stator face, an inlet discharge passage extending along a discharge path and opening to the stator face, and an outlet discharge passage extending along the discharge path and opening to the stator face. The liquid sampling valve further includes a rotor having a rotor face in fluid-tight contact with the stator face, wherein the rotor face includes a shuttle. The liquid sample transfer method includes delivering the primary stream along the primary path through the primary stator passage to fill the shuttle with the liquid sample, and rotating the rotor about an axis of rotation to bring the shuttle into fluid communication with the inlet and outlet secondary stator passages, and out of fluid communication with the primary stator passage. The method continues by delivering the secondary stream along the secondary path to transport the liquid sample with the secondary stream out from the shuttle from the outlet secondary passage, and rotating the rotor about the axis of rotation to bring the shuttle into fluid communication with the inlet and outlet discharge passages, and out of fluid communication with the inlet and outlet secondary stator passages.

BRIEF DESCRIPTION OF THE DRAWINGS

FIG. 2A is a perspective view of a liquid sampling valve of the present invention;

DETAILED DESCRIPTION OF THE PREFERRED EMBODIMENTS

Figure 1:
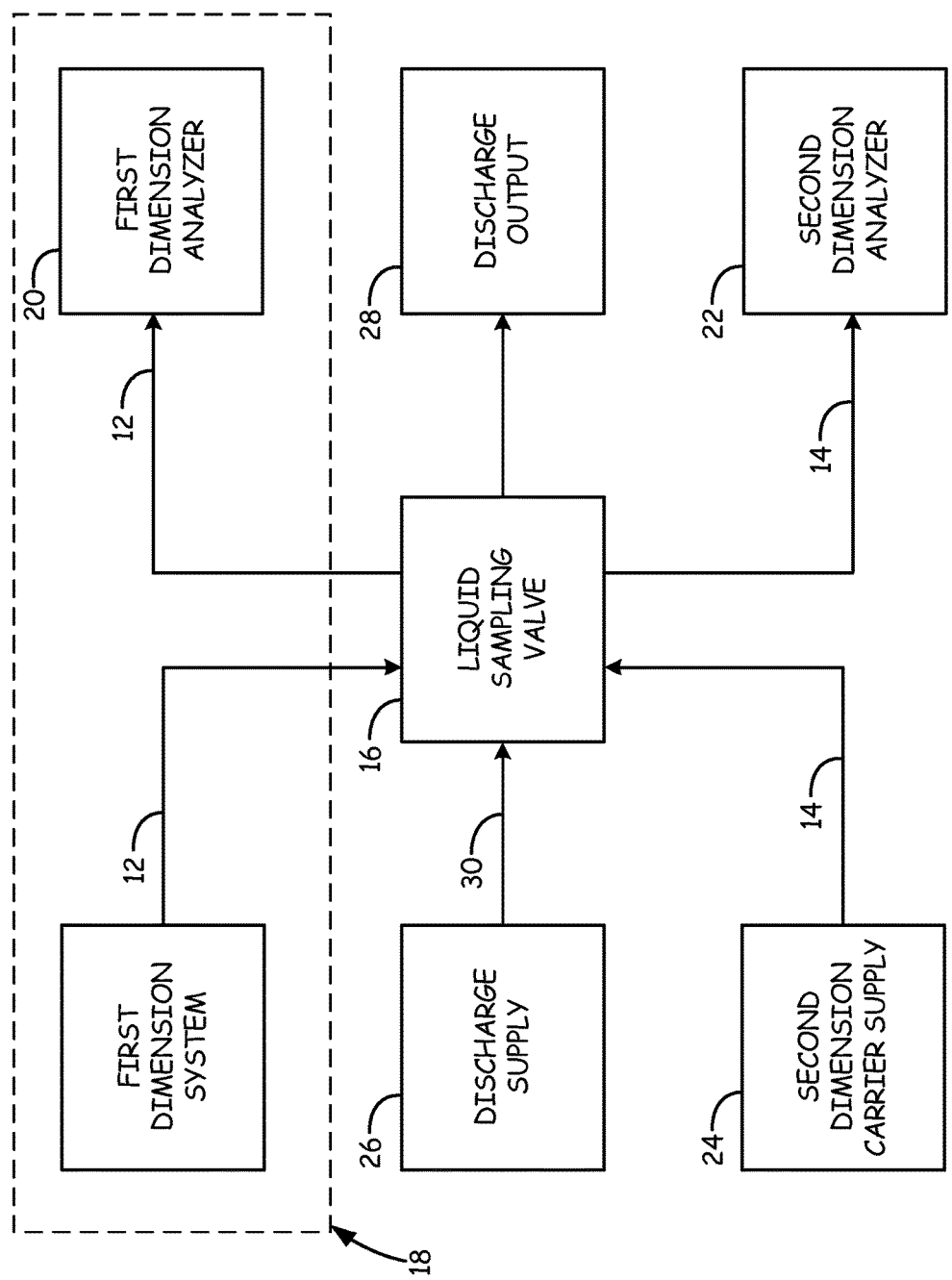
FIG. 1 is a schematic diagram of a transfer module of the present invention.
Figure 2B:
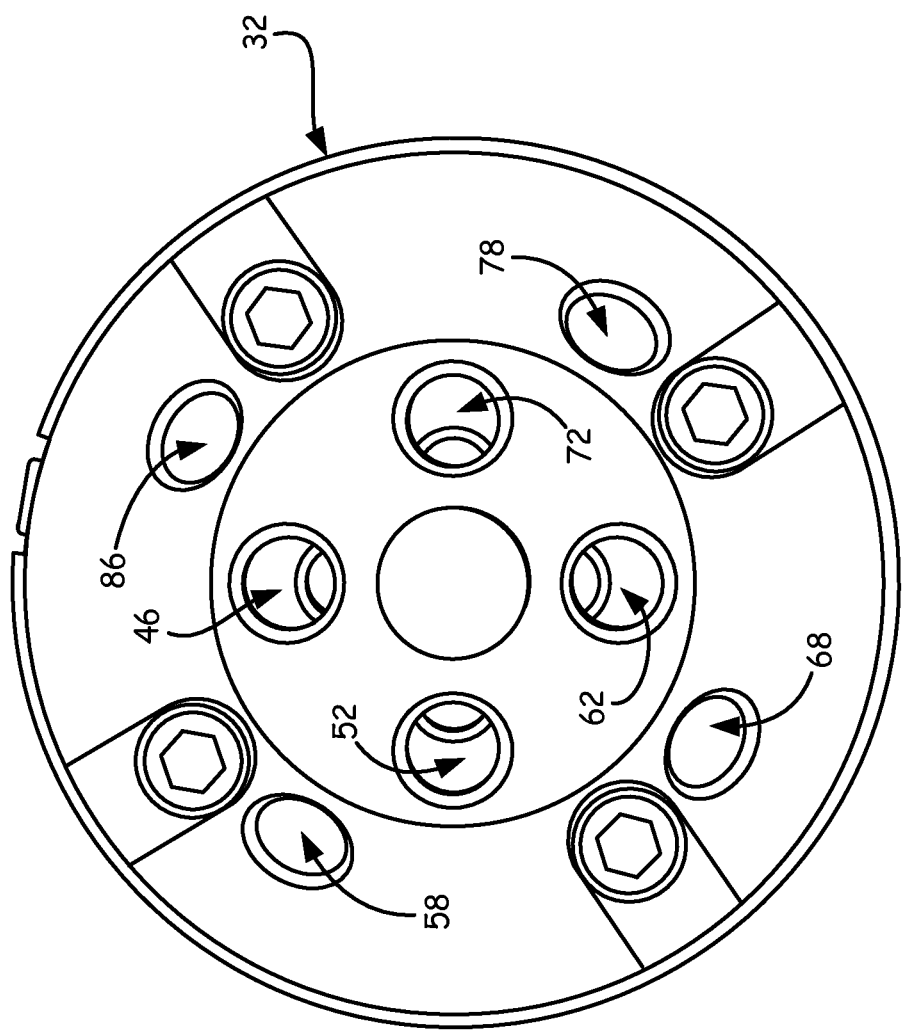
FIG. 2B is an end elevational view of the liquid sampling valve illustrated in FIG. 2A.
Figure 2C:
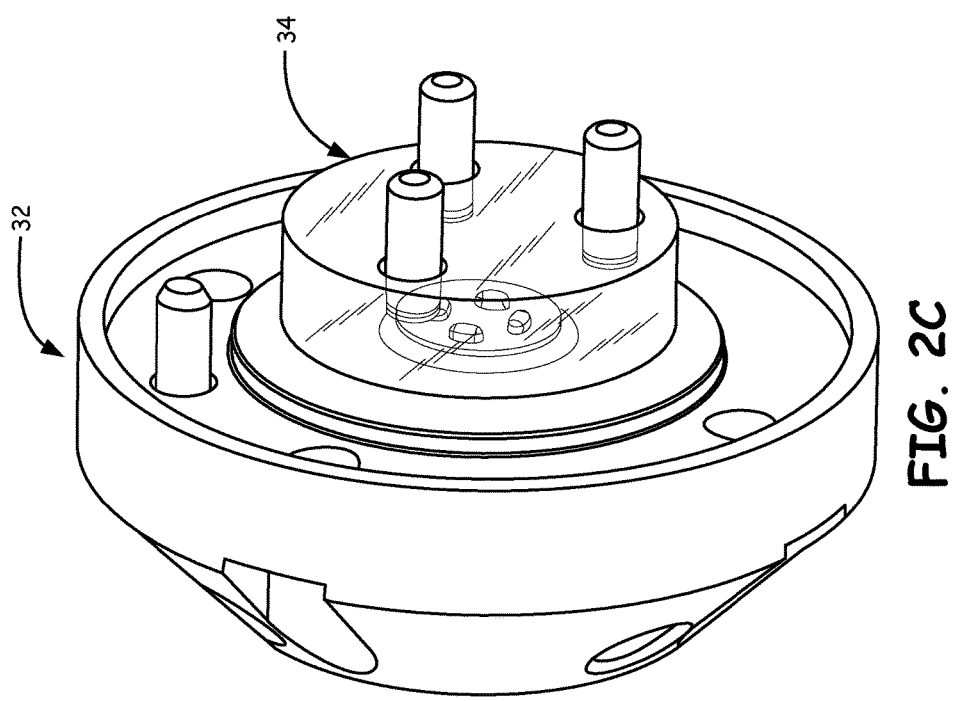
FIG. 2C is an isolation view of a stator component and a transparent rotor component of the liquid sampling valve illustrated in FIGS. 2A and 2B.
Figure 2D:
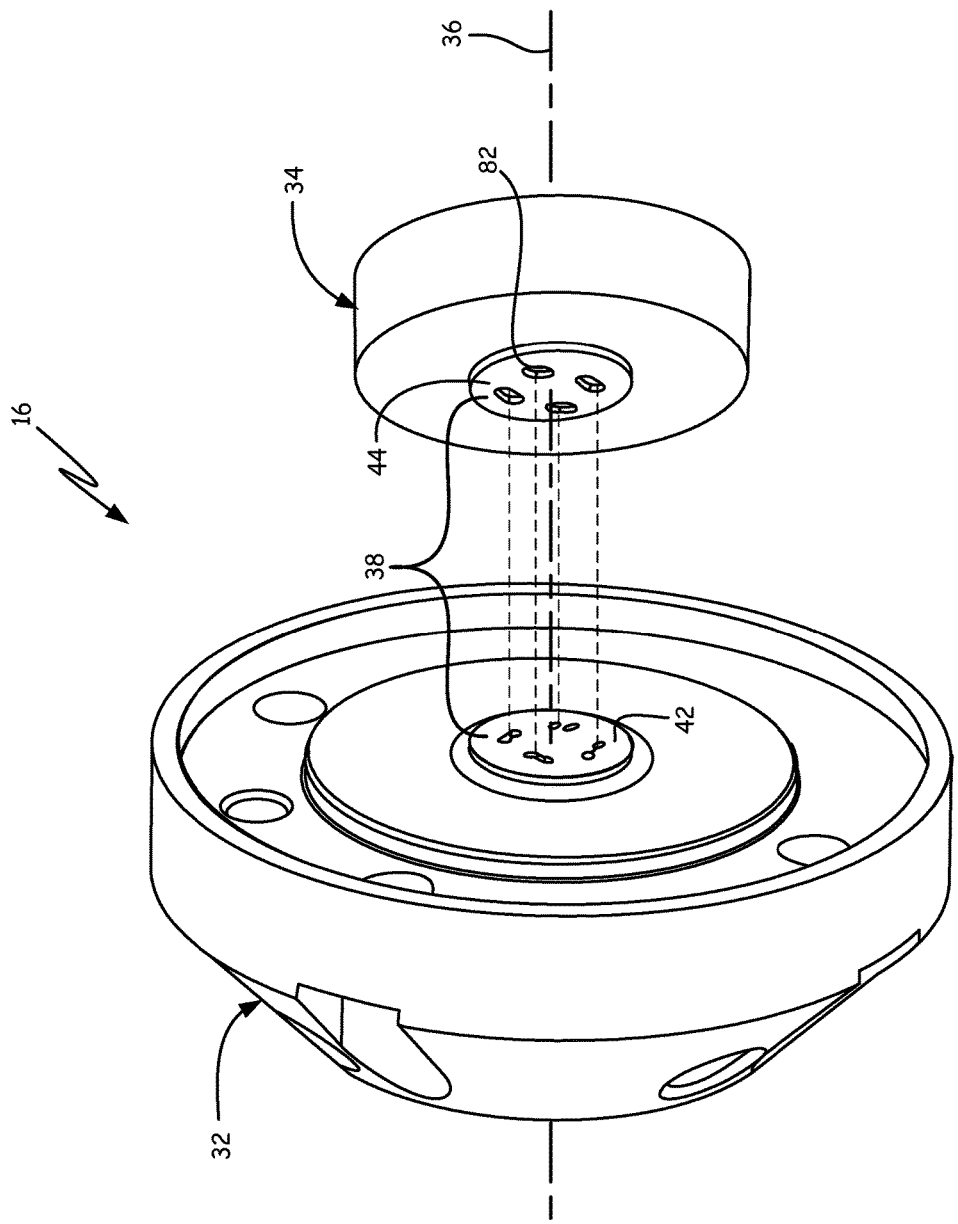
FIG. 2D is an isolation exploded view of a stator component and a rotor component of the liquid sampling valve illustrated in FIGS. 2A and 2B.

In accordance with one embodiment of the present invention, a schematic illustration of a liquid sampling system 10 is shown in FIG. 1. As described above, a common application for liquid sampling system 10 is in the transfer of a liquid sample from a primary stream 12 to a secondary stream 14, such as in a multi-dimensional liquid analysis system. Liquid sampling system 10 employs a liquid sampling valve 16 to perform the liquid sample transfer from primary stream 12 to secondary stream 14. A first dimension system 18 acts as a primary stream supply to liquid sampling valve 16, and may include at least a liquid pump for flowing first dimension liquid through liquid sampling valve 16, and, in some embodiments, to a first dimension analyzer 20. In addition to a liquid pump, first dimension system 18 may include an analyte separation mechanism, such as a liquid chromatography column for separating a first liquid into analytes within primary stream 12. First dimension system 18 may additionally include a chromatographic detector to sense the presence of analytes within primary stream 12. In some embodiments, first dimension analyzer 20 may include a fraction collection system to collect individual analytes of the primary stream 12 by fractionation.

Secondary stream 14 may be supplied to liquid sampling valve 16 for capture of a transferred liquid sample from primary stream 12, and transport to a second dimension analyzer 22 by a second dimension carrier supply 24. Typically, second dimension carrier supply 24 acts as a secondary stream supply with a second liquid pump pumping the secondary stream from a liquid reservoir through liquid sampling valve 16. In typical embodiments, the transport of the transferred liquid sample into second dimension analyzer 22 (i.e. a mass spectrometer) is accomplished by secondary stream 14 that is distinct from primary stream 12. In this manner, liquid sampling valve 16 transfers a liquid sample from primary stream 12 to a distinct secondary stream 14 that is motivated by second dimension carrier supply 24.

In order to mitigate or eliminate contamination of primary stream 12 with secondary stream 14, a moving shuttle of liquid sampling valve 16 may be rinsed or otherwise discharged of its payload from secondary stream 14 prior to returning to fluid communication with primary stream 12. Liquid sampling system 10 may therefore include a discharge stream supply 26 for driving a discharge output 28 from liquid sampling valve 16. The driving force for discharge output 28 may be in the form of a discharge stream 30 applied along a discharge path, or may instead be a vacuum applied along the discharge path to withdraw secondary stream 14 from the rotor shuttle payload prior to the rotor shuttle returning to fluid communication with primary stream 12. To supply discharge stream 30, discharge supply 26 may include a third liquid pump for pumping a third liquid through liquid sampling valve 16 along the discharge path, wherein the third liquid is different from the second liquid of secondary stream 14.

An embodiment of liquid sampling valve 16 is illustrated in FIGS. 2A-2D, including a stator 32, and a rotor 34 driven by an actuator 35, such as a stepper motor, to be rotatable with respect to stator 32 about an axis of rotation 36. Rotor 34 is mounted in valve 16 in fluid-tight contact with stator 32 at in interface 38 so that fluid is permitted to pass between stator 32 and rotor 34 without leakage outside of valve 16.

Stator 32 includes a stator face 42 that is configured for sealing engagement with rotor face 44 of rotor 34. In some embodiments, stator face 42 and rotor face 44 may be substantially planar, and placed into sealing engagement with one another through an external mounting kit (not shown). Stator 32 further includes a primary stator passage 46 extending along a primary path 48 through stator 32 and opening to stator face 42 through a first primary path port 50. An inlet secondary stator passage 52 extends along a secondary path 54 through stator 32 and opens to stator face 42 through a first port 56. An outlet secondary stator passage 58 extends along secondary path 54 through stator 32, and opens to stator face 42 through second port 60. An inlet discharge passage 62 extends along a discharge path 64 through stator 32, and opens to stator face 42 through a third port 66. An outlet discharge passage 68 extends along the path 64 through stator 32, and opens to stator face 42 through a fourth port 70. In some embodiments, an inlet sweep passage 72 extends along a sweep path 74 through stator 32, and opens to stator face 42 through a fifth port 76. Moreover, an outlet sweep passage 78 may extend along the sweep path 74 through stator 32, and may open to stator face 42 through a sixth port 80.

The passages described above are fluidic passages that provide for the passage of fluids through stator 32. Typically, such passages may be provided in sets, such as in groups of at least two, with an inlet passage and an outlet passage grouped for the conveyance of a respective fluid therethrough. It is contemplated, however, that at least primary stator passage 46 may be provided in a set of at least one passage, wherein separate inlet and outlet passages for a particular fluid conveyance is not required.

The sets of fluidic passages coordinate with one or more shuttles 82 in rotor face 44 of rotor 34 to receive a liquid aliquot in fluid communication with interface 38. Rotor 34 is rotatable with respect to stator 32 about axis of rotation 36 to sequentially move shuttle 82 into a plurality of circumaxially spaced stations in fluid alignment with respective fluidic passage sets. A primary stator passage set 84 may include primary stator passage 46 and an outlet primary stator passage 86 extending along primary path 48 through stator 32 and opening to stator face 42 through a second primary path port 88. A secondary stator passage set 90 includes inlet and outlet secondary stator passages 52, 58, and is preferably circumaxially spaced from primary stator passage set 84 at stator face 42. A discharge passage set 92 may include inlet and outlet discharge passages 62, 68, and may be circumaxially spaced from each of primary and secondary stator passage sets 84, 90 at stator face 42. A sweep passage set 94 may include inlet and outlet sweep passages 72, 78 and may be circumaxially spaced from each of primary stator passage set 84, secondary stator passage set 90, and discharge passage set 92 at stator face 42. The locations of each passage set 84, 90, 92, 94 may preferably define a station at stator face 42, wherein shuttle 82 may be moved with the rotation of rotor 34 from alignment with one station to the next. In some embodiments, rotor 34 is rotatable 360° about axis of rotation 36 so as to be sequentially brought into axial alignment with each of the stations defined by passage sets 84, 90, 92, 94 in stator face 42.

Figure 8:
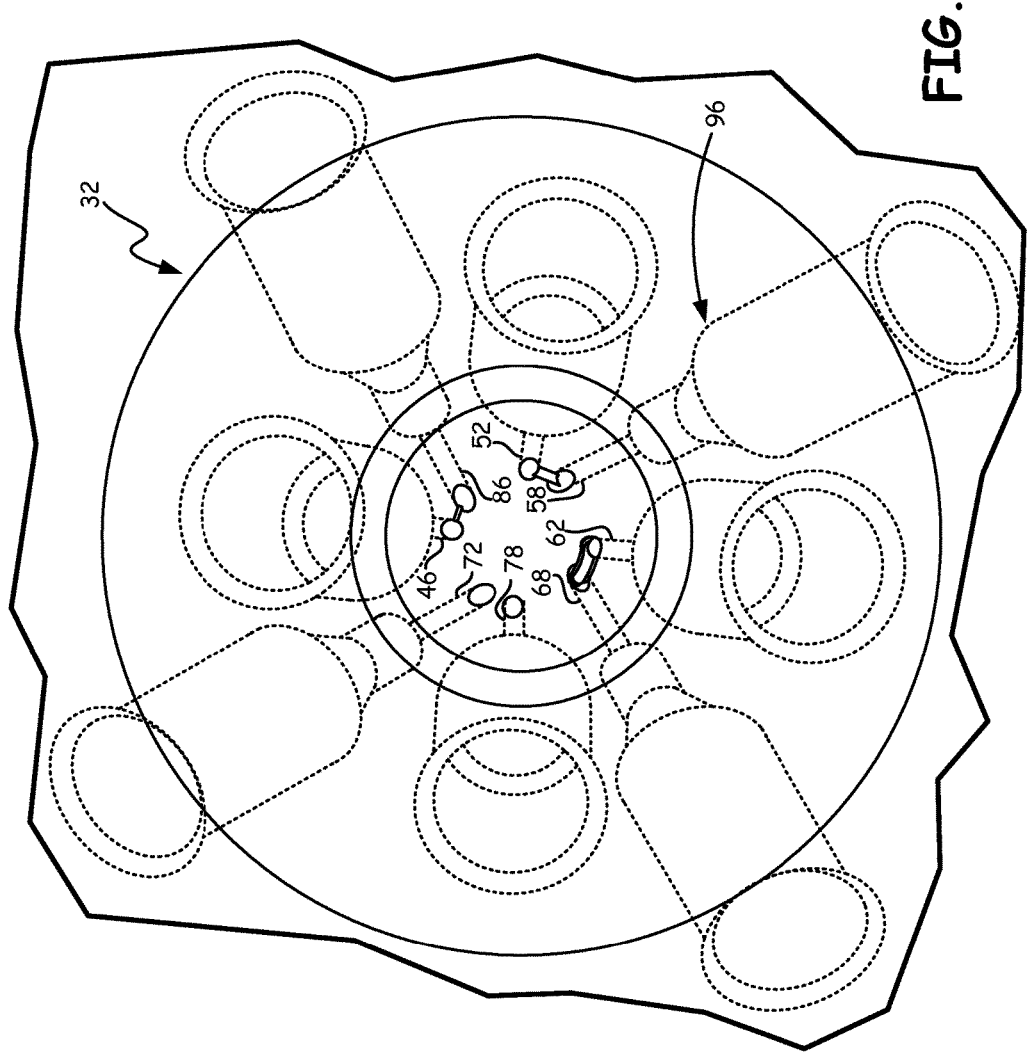
FIG. 8 is an illustration of a stator component of a liquid sampling valve of the present invention, with the stator shown as transparent to visualize the internal fluid passages in the stator component.
Figure 9:
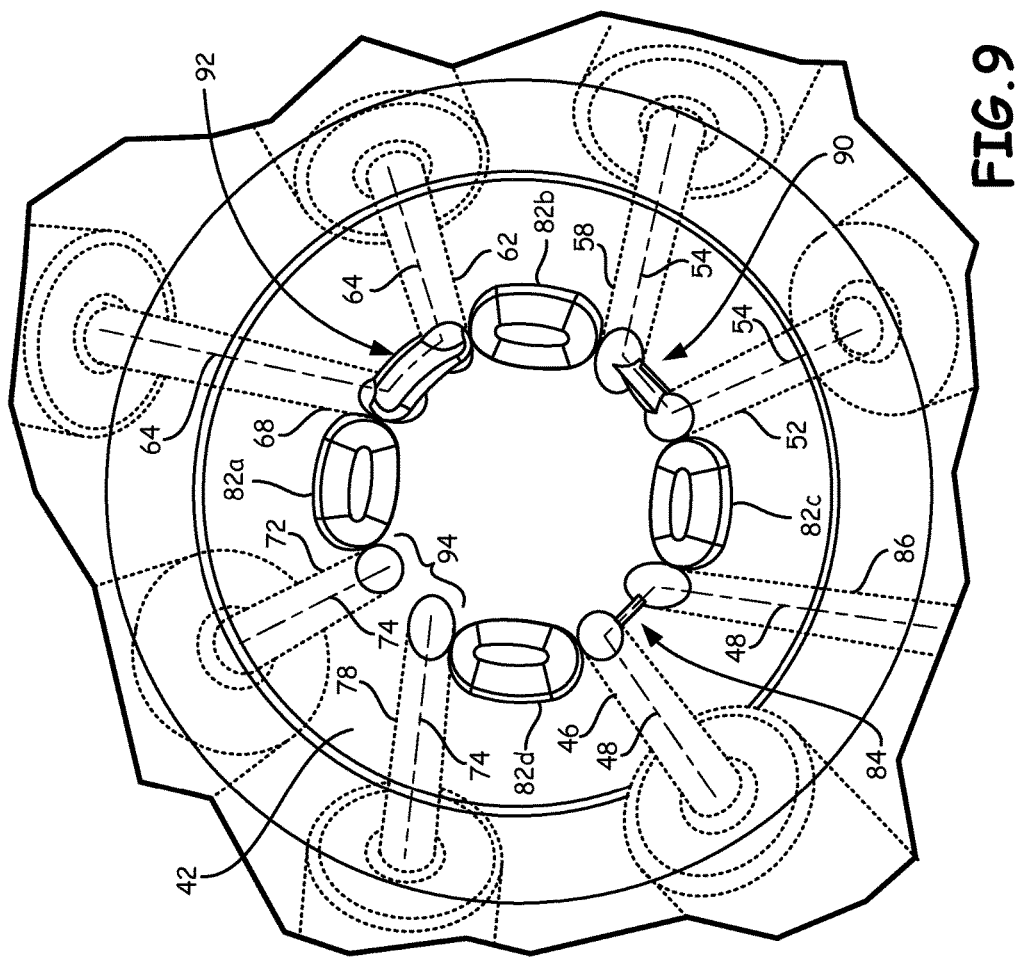
FIG. 9 is an illustration of a liquid sampling valve of the present invention with the stator and rotor components being transparent to visualize the internal fluid passages in the stator and rotor components.

As shown in FIGS. 8-9, the fluidic passages extend through stator 32 as a bore of appropriate dimension to permit the conveyance of fluids, such as those fluids commonly employed in chromatographic systems. FIGS. 8-9 illustrate stator 32 as transparent to visualize the fluidic passages extending through stator 32. The passages may be linear or non-linear, and extend away from stator face 42 to respective fluidic connections 96 fluidly coupling valve 16 to liquid sampling system 10. A typical fluidic connection 96 may include a nut and ferrule arrangement that is known to those of ordinary skill in the art.

Figure 4:
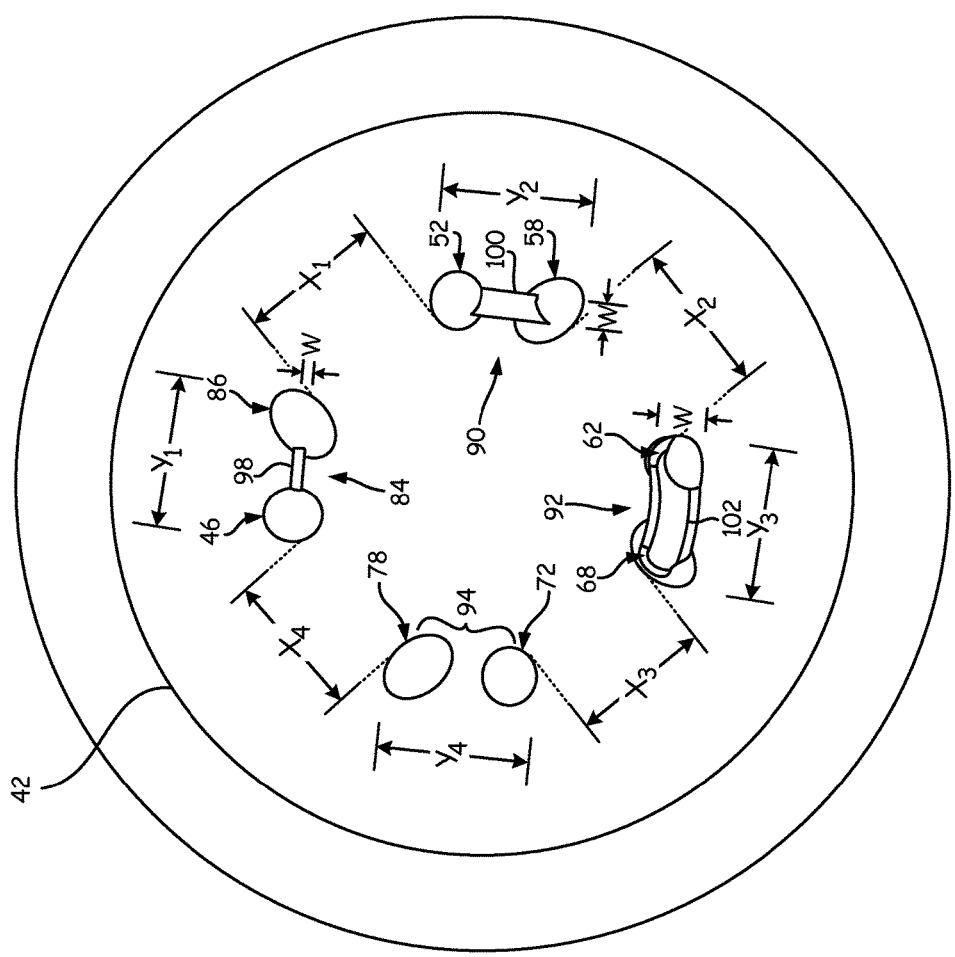
FIG. 4 is an enlarged view of a portion of the stator component illustrated in FIG. 3.
Figure 5:
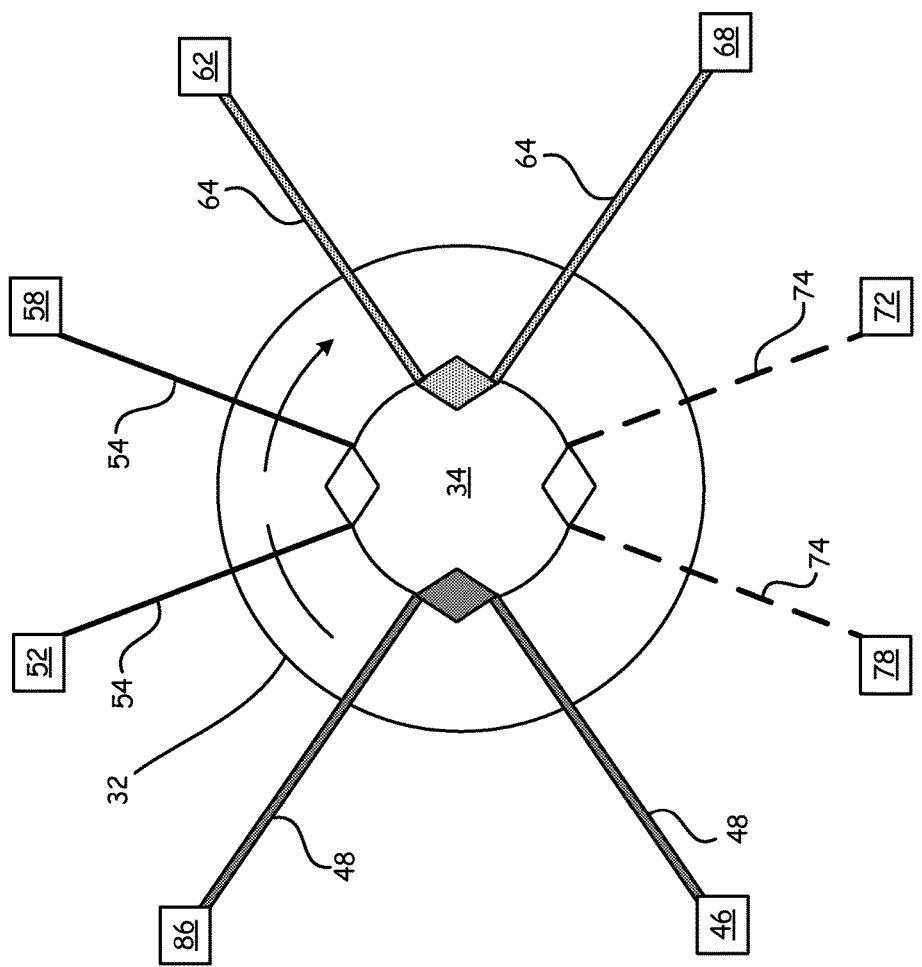
FIG. 5 is a schematic diagram of a liquid sampling valve of the present invention.
Figure 6:
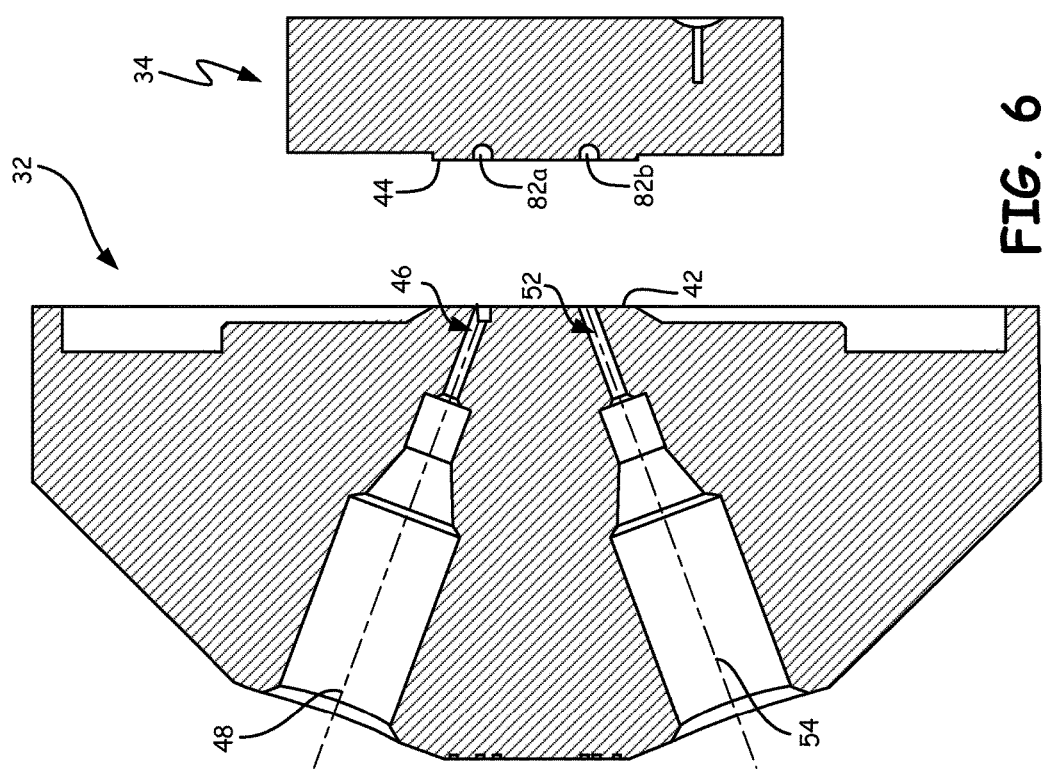
FIG. 6 is a cross-sectional exploded view of a stator component and a rotor component of a liquid sampling valve of the present invention.
Figure 7:
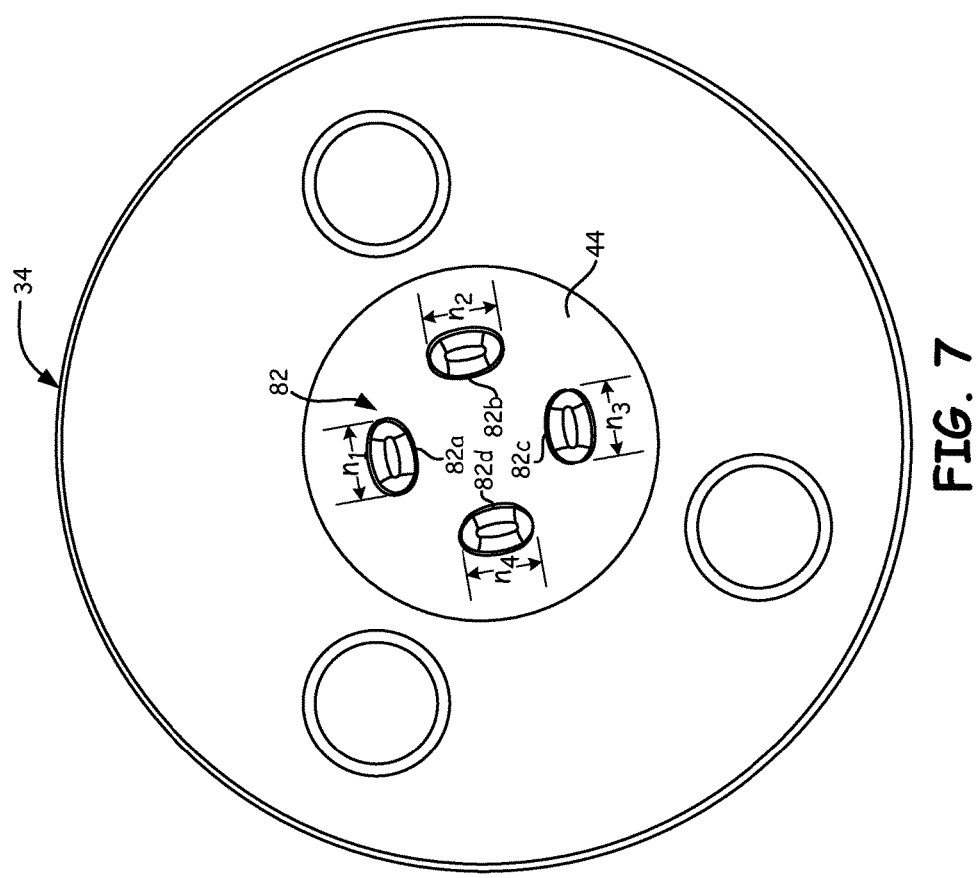
FIG. 7 is an isolation elevational view of a rotor component of a liquid sampling valve of the present invention.

In some embodiments of the invention, the respective fluid passages of one or more of passage sets 84, 90, 92, 94 may be fluidly connected to form a continuous fluid channel along the respective fluid path through stator 32 to interface 38 along a first leg, and then from interface 38 back through stator 32 along a second leg of the fluid path. Such a fluid connection among the fluidic passages in a given passage set permits continuous fluid flow along the respective fluid path when stator face 42 is sealed to rotor face 44, regardless of the circumaxial position of shuttle 82. It has been determined that a second dimension chromatographic analysis may be benefited with continuous flow of at least secondary stream 14 to second dimension analyzer 22. Benefits may also be derived from continuous flow of primary stream 12 through liquid sampling valve 16. Mass spectrometers, which are commonly utilized as second dimension analyzers 22, are susceptible to inaccurate analysis, and possibly damage, in a discontinuous feed flow regime. Therefore, it is desirable to supply second dimension analyzer 22 with a continuous flow of secondary stream 14. To do so, however, secondary stream 14 must pass through liquid sampling valve 16 continuously, regardless of the position of shuttle 82 in rotor face 42. When shuttle 82 is between stations on stator face 42, rotor face 44 acts as a block to fluid passage at interface 38. Shuttle 82 is therefore provided to establish a fluid connection at interface 38, as well as to transport a liquid aliquot from one station to the next. One approach for establishing a fluid connection among respective fluid passages in a passage set in the absence of shuttle 82 is the provision of a bypass channel in stator 32 fluid connecting respective fluid passages. An example embodiment is illustrated in FIG. 4, wherein a primary bypass channel 98 is disposed in stator 32 to fluidly connect primary stator passage 46 to outlet primary stator passage 86. A secondary bypass channel 100 is likewise provided in stator 32 to form a fluid connection between inlet and outlet secondary stator passages 52, 58. A discharge bypass channel 102 may be provided in stator 32 to form a fluid connection between inlet discharge passage 62 and outlet discharge passage 68. In the embodiment illustrated in FIG. 4, no bypass channel is provided for sweep passage set 94. However, it is contemplated that a sweep bypass channel 104 may be included for sweep passage set 94 to establish a fluid connection in stator 32 between inlet and outlet sweep passages 72, 78. It is to be understood that any, all, or none of the fluid passages within any, all, or none of passage sets 84, 90, 92, 94 may have a fluid connection in stator 32, such as with respective bypass channels 98-104. The purpose of bypass channels 98-104, as described above, is to establish, in stator 32, a fluid connection among respective fluid passages. It is contemplated that bypass channels 98-104 may be of any appropriate size or configuration to suitably permit bypass fluid flow between respective fluid passages, and along a respective fluid path. Bypass channels 98-104 may, for example, be grooves in stator face 42 extending between respective ports of the fluid passages. In such an embodiment, the bypass channel may be open to interface 38, but enclosed by rotor face 44. In other embodiments, one or more of bypass channels 98-104 may be fully enclosed within stator 32. The channel widths "W" are shown in varying degrees in FIG. 4, representative of example widths relative to respective ports at stator face 42. Channel widths "W" may be between 5-100% of the diameters of the corresponding ports of the respective fluid passages being fluidly connected by the bypass channels. In some embodiments, therefore, bypass channel widths "W" may be between 5-39 mils (125-750 micrometers). A fluid connection between respective fluid passages may be formed in stator 32 at a merge region merging the respective fluid passages. Preferably, such merge regions may be at or near stator face 42, and in fluid connection with interface 38. In such embodiments, no distinct bypass channel is required to establish a fluid connection in stator 32 between respective fluid passages.

Passage sets 84, 90, 92, 94 are preferably circumaxially spaced apart about axis of rotation 36 by respective circumaxial spacing dimensions $X_1$-$X_4$. It is contemplated that such circumaxial spacing dimensions $X_1$-$X_4$ may be equal or inequal, but are each preferably greater than a corresponding length dimension $N_1$ of shuttle 82 in rotor 34. Preferably, each of circumaxial spacing dimensions $X_1$-$X_4$ are greater than shuttle length dimension $N_1$ to an extent sufficient to prevent cross-flow between adjacent passage sets 84, 90 92, 94 as shuttle 82 is being rotated from alignment with a first station to a second station. For example, shuttle 82 may be initially positioned at a first station in alignment with primary stator passage set 84 to receive a liquid aliquot of primary stream 12. To transfer such liquid aliquot to secondary stream 14, rotor 34 is rotated about axis of rotation 36 with respect to stator 32 so that shuttle 82 is moved from the first station to a second station in alignment with secondary stator passage set 90. Secondary stream 14 traveling along secondary path 54 then acquires the liquid aliquot of primary stream 12 from shuttle 82 while at the second station. It is desired that volumes of the liquid aliquot be sampled into secondary stream 14 at known time intervals for analysis purposes. Therefore, shuttle 82 preferably does not provide a fluid communication link between respective distinct passage sets, such as primary stator passage set 84 and secondary stator passage set 94, as it is rotated between respective stations. Otherwise, fluid flowing at a first passage set would be able to pass into the fluid flowing at another passage set while shuttle 82 is in route between stations. At some point during the travel of shuttle 82 between such stations, therefore, shuttle 82 should be in fluid communication with neither of the distinct passage sets. FIG. 9 is a schematic illustration of an intermediate rotor position with respect to stator 32 wherein shuttles 82a-82d are each out of the flow path of any passage set 84, 90, 92, 94. In some embodiments, circumaxial spacing dimensions $X_1$-$X_4$ are each at least 0.25 millimeters greater than shuttle length $N_1$. As will be described in greater detail hereinbelow, rotor face 44 may be provided with a plurality of circumaxially spaced shuttles 82a-82d, each having a shuttle length $N_1$-$N_4$, which may be equal or inequal. In such an embodiment, each of circumaxial spacing dimensions $X_1$-$X_4$ is preferably greater than the largest of shuttle lengths $N_1$-$N_4$, to prevent cross-flow between any passage sets 84, 90, 92, 94 during the rotatable operation of rotor 34. An example shuttle length $N_1$ is 1.5 millimeters, with the corresponding circumaxial spacing dimension $X_1$-$X_4$ in stator face 42 being, for example, at least 1.75 millimeters.

Passage set length dimensions $Y_1$-$Y_4$ of respective passage sets 84, 90, 92, 94 are preferably substantially equal to, or slightly larger than shuttle lengths $N_1$-$N_4$. It is contemplated that passage set lengths $Y_1$-$Y_4$ may be equal or inequal, and may be determined by the designer per application.

Shuttles 82a-82d may be in the form of depressions in rotor face 44, and may be of equal or inequal volume. Example volumes defined within shuttles 82a-82d may be between 10-1000 nanoliters, with the shapes of shuttles 82a-82d being appropriate to effectively receive and discharge liquid aliquots therefrom, as well as to establish and maintain desired fluid flow characteristics when positioned at a respective station in alignment with a corresponding fluid passage set 84, 90, 92, 94 of stator 32. It is contemplated that one or more shuttles 82 may be provided in rotor face 44. The one or more shuttles 82a-82d are movable with rotor 34 into a plurality of circumaxially spaced stations with the rotation of rotor 34 about axis of rotation 36. A first station aligns a shuttle 82a in fluid communication with primary path 48 at first primary path port 50. Rotating rotor 30 by a predetermined extent about axis of rotation 36 moves shuttle 82a to a second station aligning shuttle 82a in fluid communication with secondary path 54 at first and second ports 56, 60. Further rotation of rotor 34 moves shuttle 82a to a third station aligning shuttle 82a in fluid communication with discharge path 64 at third and fourth ports 66, 70. In some embodiments, further rotation of rotor 34 moves shuttle 82a to a fourth station aligning shuttle 82a in fluid communication with sweep path 74 at fifth and sixth ports 76, 80. In some embodiments, each of the stations described above are separated by a 90° rotation about axis of rotation 36, such that rotor 34 is rotated 360° about axis of rotation 36 to cycle shuttle 82a through sequential alignment with respective passage sets 84, 90, 92, 94 at the circumaxially spaced stations. The cycle is repeatable through continued rotation about axis of rotation 36.

Though just one shuttle 82a in rotor face 44 may fulfill the necessary functions of liquid sampling valve 16, the rate of sampling of primary stream 12 may be such that sufficient time may not exist for a single shuttle 82a to transit through each of the designated stations. In an example situation wherein one sample per second is to be taken from primary stream 12 to be transferred to second stream 14, a single shuttle 82a must be drive through each station in a total of one second, pausing at each station for a time sufficient to exchange the appropriate fluids. The limitations inherent therein may not permit a sampling interval of one sample per second from primary stream 12 with only a single shuttle 82a. The rate of rotation of rotor 32 can, however, be significantly reduced with the provision of additional shuttles 82b-82d. In the same example with a sampling interval of one sample per second, a rotor face 44 having four equally circumaxially spaced shuttles 82a-82d could accomplish the desired sampling rate with a rotational rate of one revolution per four seconds (15 rpm). The significantly slower rotational rate of rotor 34 permits longer dwell times at each distinct shuttle station in the valve cycle.

Figure 10:
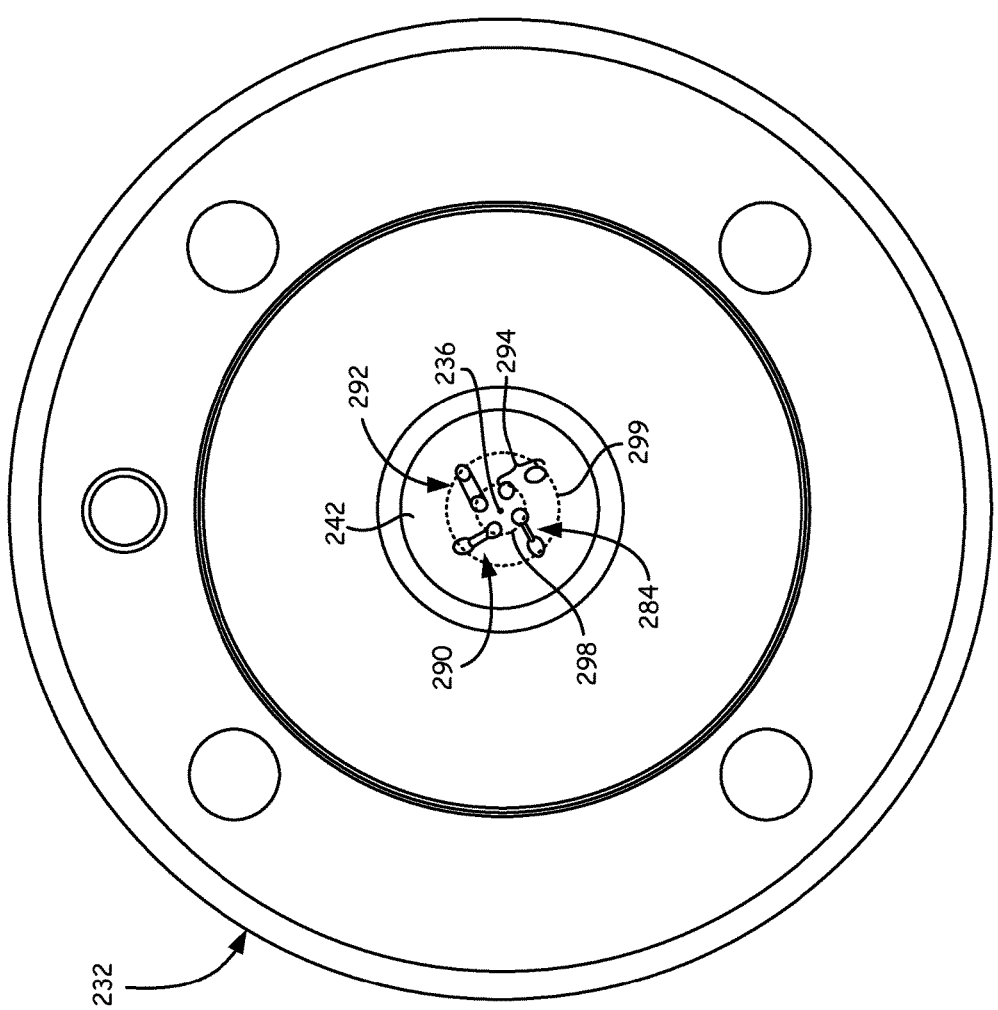
FIG. 10 is an end elevational view of an alternate stator component of a liquid sampling valve of the present invention.
Figure 11:
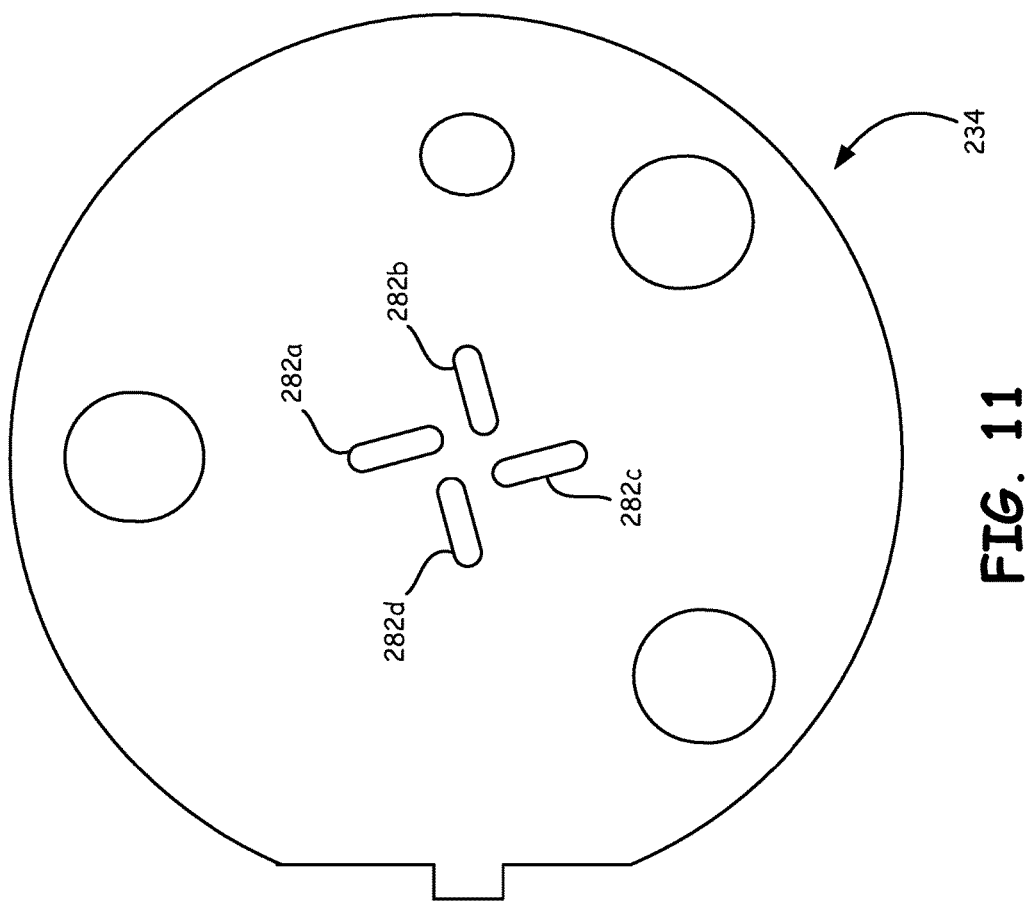
FIG. 11 is an end elevational view of an alternate rotor component of a liquid sampling valve of the present invention.
Figure 12:
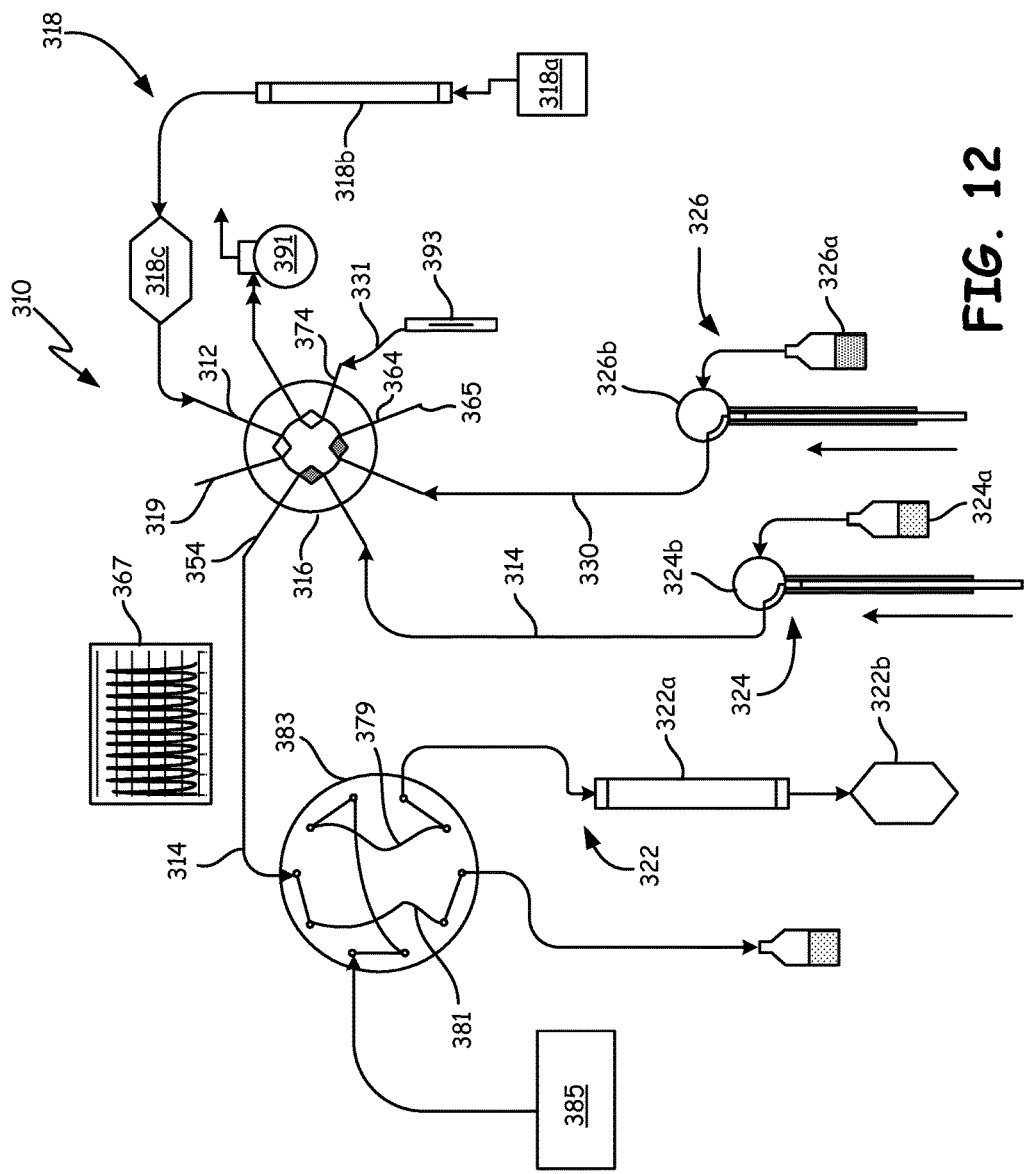
FIG. 12 is a schematic diagram of a two dimensional liquid analysis system employing a liquid sampling system of the present invention.

An alternative fluid passage set arrangement of the present invention is illustrated in FIG. 10, wherein stator 232 includes a stator face 242 with passage sets 284, 290, 292, 294 in a modified orientation circumaxially spaced about axis of rotation 236. A corresponding alternate arrangement for rotor 234 is shown in FIG. 11, with shuttles 282a-282d in rotor face 244 having a similarly modified orientation about axis of rotation 236. In this orientation, passage sets 284, 290, 292, 294 may be circumaxially spaced apart by larger dimensions $X_1$-$X_4$ than that illustrated in FIG. 4, so as to obtain greater sealing surface between adjacent passage sets 284, 290, 292, 294. In this embodiment, each passage set includes a radially inward passage port and a radially outward passage port, with respect to axis of rotation 236. An angular relationship is therefore developed between respective ports in a passage set 284, 290, 292, 294 with reference to inner and outer circumferential boundaries 289, 299 passing through the respective inner and outer passage ports.

Liquid sampling valve 16 may accordingly be provided to periodically transfer a liquid aliquot from primary stream 12 to secondary stream 14, with typical primary stream sampling rates being between one sample each five seconds to one sample each 0.1 second. In the illustrated embodiment, a first shuttle 82 is positioned at a first station aligning shuttle 82 in fluid communication with primary path 48 at primary stator passage set 84 to receive a liquid aliquot from primary stream 12 being flowed along primary path 48. Shuttle 82 is filled with the liquid aliquot as a consequence of an appropriate dwell time of shuttle 82 at the first station, along with a continuous flow of primary stream 12 through primary stator passage set 82 along primary path 48. Once a predetermined dwell period, which is a fraction of a rotor cycle time, is elapsed, a stepper motor or the like is actuated to rotate rotor 34 by a predetermined extent about axis of rotation 36 within a transfer period. In the illustrated embodiment, the extent of rotation may be 90° to move shuttle 82 from the first station to a second station aligning shuttle 82 in fluid communication with the secondary path 54 at secondary stator passage set 90. The transfer period may be assigned as necessary for the application, and within the limits of the driving force rotating rotor 34, and may typically be less than about 0.1 seconds. Preferably, the transfer period is substantially less than the dwell period of the rotor cycle to maximize the time for shuttle 82 at each station in the cycle, thereby successfully transferring fluid to and from shuttle 82.

As shuttle 82 arrives at the second station in fluid communication with secondary path 54 and secondary stator passage set 90, secondary stream 14 being flowed along secondary path 54 flushes the liquid aliquot sample from shuttle 82 into secondary stream 14. In this manner, the liquid aliquot sample from primary stream 12 is transferred to secondary stream 14 for analysis at second dimension analyzer 22. Secondary stream 14 carries the liquid aliquot sample from shuttle 82 through outlet secondary stator passage 58 along secondary path 54 out of liquid sampling valve 16, and beyond to second dimension analyzer 22, as shown in FIG. 1. In contrast to conventional liquid sampling valves, which operate a rotor through a back and forth switching path that results in the flushing carrier fluid of secondary stream 14 in the rotor shuttle at the time of rotor switching being transported back into fluid connection with primary stream 12, rotor 34 of the present invention is actuated to rotate shuttle 82 from the second station to a third station in fluid communication with discharge path 64 at discharge passage set 92. As shuttle 82 arrives at the third station, a discharge operation may be applied to remove the volume of secondary stream 14 retained in shuttle 82 from the second station. As described above, it is desirable to avoid contamination of primary stream 12 with the carrier fluid of secondary stream 14. In one example discharge operation, a liquid compatible with primary stream 12 may be utilized as a carrier fluid in discharge stream 30 to flush out the volume of secondary stream in shuttle 82 carried to the third station from the second station. In some embodiments, the carrier fluid of discharge stream 30 may be identical to, or compatible with the solvent carrier fluid in primary stream 12 carrying the analytes for analysis at first and second analyzers 20, 22. The dwell period at the third station is preferably sufficient to enable discharge stream 30 to satisfactorily flush the secondary stream volume from shuttle 82 out through outlet discharge passage 68 to a waste container.

Another discharge operation that may be employed at the third station is a pressurized gas flow as discharge stream 30 forcing the secondary stream volume to discharge from shuttle 82 under a positive gas pressure applied through inlet discharge passage 62 to force the liquid volume out through outlet discharge passage 68. A further example discharge operation may be in the application of a negative pressure, such as an applied vacuum, applied to the secondary stream volume in shuttle 82 at the third station through outlet discharge passage 68. In this case, the negative pressure "withdraws" the liquid volume from shuttle 82, and is replaced by ambient gas or other fluid supplied to inlet discharge passage 62 along discharge path 64. In each of these cases, the secondary stream volume is substantially discharged from shuttle 82 prior to shuttle 82 being returned to fluid communication with primary stream 12 at the first station, thereby mitigating or eliminating contamination of primary stream 12 that typically occurs in conventional liquid sampling valve apparatus.

In the illustrated embodiment, a fourth station is provided to which shuttle 82 may be rotated for fluid communication with sweep path 74. Applicants contemplate that a sweep operation may be applied to shuttle 82 subsequent to the discharge operation to further mitigate the potential of contamination of primary stream 12 at the first station, as well as to enhance the overall operation of liquid sampling valve 16. An example sweep operation includes supplying a pressurized gas, such as an inert gas or other gas compatible with primary stream 12, along sweep path 74 through inlet sweep passage to push any residual discharge stream volume and/or secondary stream volume out from shuttle 82 through outlet sweep passage 78. Another sweep operation contemplated by the present invention is the application of a negative pressure to shuttle 82 at the fourth station through outlet sweep passage 78 to "withdraw" the liquid contents of shuttle 82 when at the fourth station. Makeup fluid, such as ambient gas, or a supplied gas compatible with primary stream 12, may be permitted to flow along sweep path 74 through inlet sweep passage 72 to replace the liquid volume so removed from shuttle 82 at the fourth station.

Upon the expiration of a predetermined dwell period, rotor 34 is actuated to rotate about axis of rotation 36 to bring shuttle 82 from the fourth station to the first station, thereby completing a valve cycle. Preferably, rotor actuation is in a single rotational direction 360° about axis of rotation 36. It has been found that unidirectional rotation of rotor 34 with respect to stator 32 can enhance valve component and motor life expectancies. However, it is to be understood that the present invention is not limited to unidirectional rotation of rotor 34 with respect to stator 32, and that the shuttle stations need not be in sequential order in a circumaxial direction about axis of rotation 36. Liquid sampling valve 16 preferably includes at least three shuttle stations, and may include more than the four stations described in the illustrated embodiments. A primary feature of the liquid sampling valve of the present invention, however, is at least one shuttle station for flushing and/or rinsing shuttle 82 to remove the liquid volume of secondary stream 14 from shuttle 82 prior to the return of shuttle 82 into fluid communication with primary stream 12. The valve cycle described above may be referred to as "sampled, transferred, washed, and dried". The station procedures described above may occur when a shuttle 82a-82d is brought into fluid communication with a respective passage set 84, 90, 92, 94 at the corresponding shuttle station. Thus, a second liquid aliquot sample may be filled into shuttle 82d while the first liquid aliquot sample previously filled into shuttle 82a is transferred to secondary stream 14 at the second station. Moreover, a secondary stream liquid volume retained in shuttle 82b may then be discharged as shuttle 82b is brought into fluid communication with discharge stream 30 at discharge passage set 92. Additionally, any remaining liquid volume in shuttle 82c may be swept by a sweep procedure at the fourth station. In this manner, multiple simultaneous operations may be occurring at liquid sampling valve 16 at any one time, particularly during the dwell periods of the valve cycle.

In typical embodiments, the dwell periods at each of the shuttle stations is equal, and the transfer period rotating shuttles 82a-82d between sequential stations may also be equal. However, such dwell periods may be inequal, and such transfer periods may be inequal, as needed or desired per the application.

The bypass channels 98, 100, 102, 104 described above permit continuous flow of the respective primary, secondary, discharge, and sweep streams, regardless of the relative rotational position of rotor face 44 with respect to stator face 34. The only flow change occurs when shuttles 82a-82d are rotated into a respective station, wherein stream flows pass into communication with such shuttles 82a-82d. It is also contemplated that a plurality of sampling stations and transfer stations, such as that described above with respect to first and second stations, may be included in liquid sampling valve 16 of the present invention.

An example liquid sampling system 310 of the present invention involves a two dimensional liquid chromatography system with transfer of a first dimension sample into a second dimension HPLC system for orthogonal analysis. A first dimension HPLC system 318 includes a sample source 318a, an HPLC column 318b, and a chromatographic detector 318c. The eluting sample from chromatographic detector 318c flows into liquid sampling valve 316 as a primary stream 312. Rotor 334 of liquid sampling valve 316 may be operably rotated at a speed sufficient to sample each peak eluting from chromatographic detector 318c at least three times, but preferably at least seven times. The rate of rotor rotation is then related to the expected peak width in seconds for a peak eluting from the first dimension chromatographic detector 318c. For example, a chromatographic peak spanning seven seconds and eluting at one ml/min (17 µl/s) from the first dimension system 318 may preferably be sampled seven times (once per second). In an example embodiment in which each shuttle 382 is configured to contain one microliter, the dwell period at each shuttle station may be 58 milliseconds. In this example situation, therefore, liquid sampling valve 16 may be operated so that primary stream 312 is sampled once per second, with a dwell period at each shuttle station of at least 58 milliseconds. Primary stream 312 not transferred by a respective shuttle 382 flows along primary path 348 through outlet primary stator passage 386 to waste 319. Upon the expiration of the dwell period, rotor 332 is rotated 90° about axis of rotation 336 to bring shuttle 382 to a second station into fluid communication with secondary stream 314 flowing along secondary path 354 under the motivation of second dimension carrier supply 324, which includes a second dimension carrier fluid reservoir 324a and a second dimension carrier fluid pump 324b.

Secondary stream 314 carries the liquid aliquot sample from primary stream 312 along secondary path 354 to a sample loop 381 of valve 383, which may be a multi-port valve configured as a dual-loop injector to second dimension HPLC system 322.

In the illustrated embodiment, second dimension HPLC system 322 includes an HPLC pump 385, dual-loop injection valve 383, chromatographic separation column 322a and detector 322b, which may be a mass spectrometer configured to perform a rapid separation. For comprehensive sampling of primary stream 312, sample loops 379 and 381 of valve 383 are preferably sized to accommodate a secondary stream flow rate in milliliters per minute in the time selected for the second dimension chromatograph to be developed and the HPLC column 322a and system to be re-equilibrated. In an example scenario in which one sample is taken each second from primary stream 312, and the second dimension separation and re-equilibration occurs in 20 seconds, a total volume of 20 microliters may be transferred from liquid sampling valve 316 to valve 383. Therefore, a minimum flow rate of 20 microliters per 20 seconds from second dimension carrier pump 324b is established. Computational flow dynamics indicate that one microliter of liquid dilutes to two microliters during the flush out of shuttle 382 from liquid sampling valve 316, a minimum flow rate for second dimension carrier pump 324b may become 40 microliters in 20 seconds for quantitative sample transfer under the above conditions. Such a flow rate causes sample to "stack" in sequence between liquid sampling valve 316 and injector valve 383, as schematically represented by a detector trace 367. Sample loops 379, 381 in this instance, may be sized to accommodate at least 40 microliters. Since a gradient may be preferred for the separation at second dimension column 322a, it may also be desirable that the second dimension carrier be a weak solvent for a second dimension column 322a, and most desirably the same solvent as the weak solvent supplied to HPLC pumping system 385. Upon the lapse of a dwell period permitting the transfer of liquid aliquot sample of primary stream 312 into secondary stream 314, an additional 90° rotor rotation moves shuttle 382 into a third station for discharging fluid in shuttle 382 from second dimension carrier reservoir 324a. Discharge supply 326 includes a discharge fluid reservoir 326a and a discharge pump 326b, with the discharge fluid preferably being selected to be miscible with the components of the fluid contained within second dimension carrier fluid. In one embodiment, at least five times the shuttle volume is flowed through shuttle 382 during the dwell period while shuttle 382 is positioned at third station. Discharge fluid is flushed along discharge path 364 to waste 365.

Rotor 334 of liquid sampling valve 316 may be further rotated to a fourth station at which an applied vacuum evacuates material contained within flushed shuttle 382 from the third station. A vacuum pump 391 acts to remove any volume of solvent remaining in shuttle 382 after flushing with discharge stream 330. A flow restrictor 393 sufficiently limits the flow rate of sweep stream 331 along sweep path 374 to enhance evaporation of any solvent contained in shuttle 382 by lowering the pressure in 382 to near the vapor pressure of the discharge fluid. Moreover, gas flow at sweep stream 331 displaces any contents in shuttle 382 to vacuum pump 391. When the flow of gas through flow restrictor 393 is limited to a small percentage of the capacity of vacuum pump 391, a partial vacuum is developed within shuttle 382 at this fourth station. Upon valve rotation to the first station, the partial vacuum contained within shuttle 382 enhances the filling rate of liquid aliquot sample from primary stream 312 into shuttle 382. As illustrated in the diagram of FIG. 9, each of the passage sets 384, 390, 392, 394 may be associated with an individual distinct shuttle station. In the case where four shuttles 382a-382d are provided in rotor face 344, each shuttle 382a-382d is exposed in turn to each passage set 384, 390, 392, 394.

Figure 13:
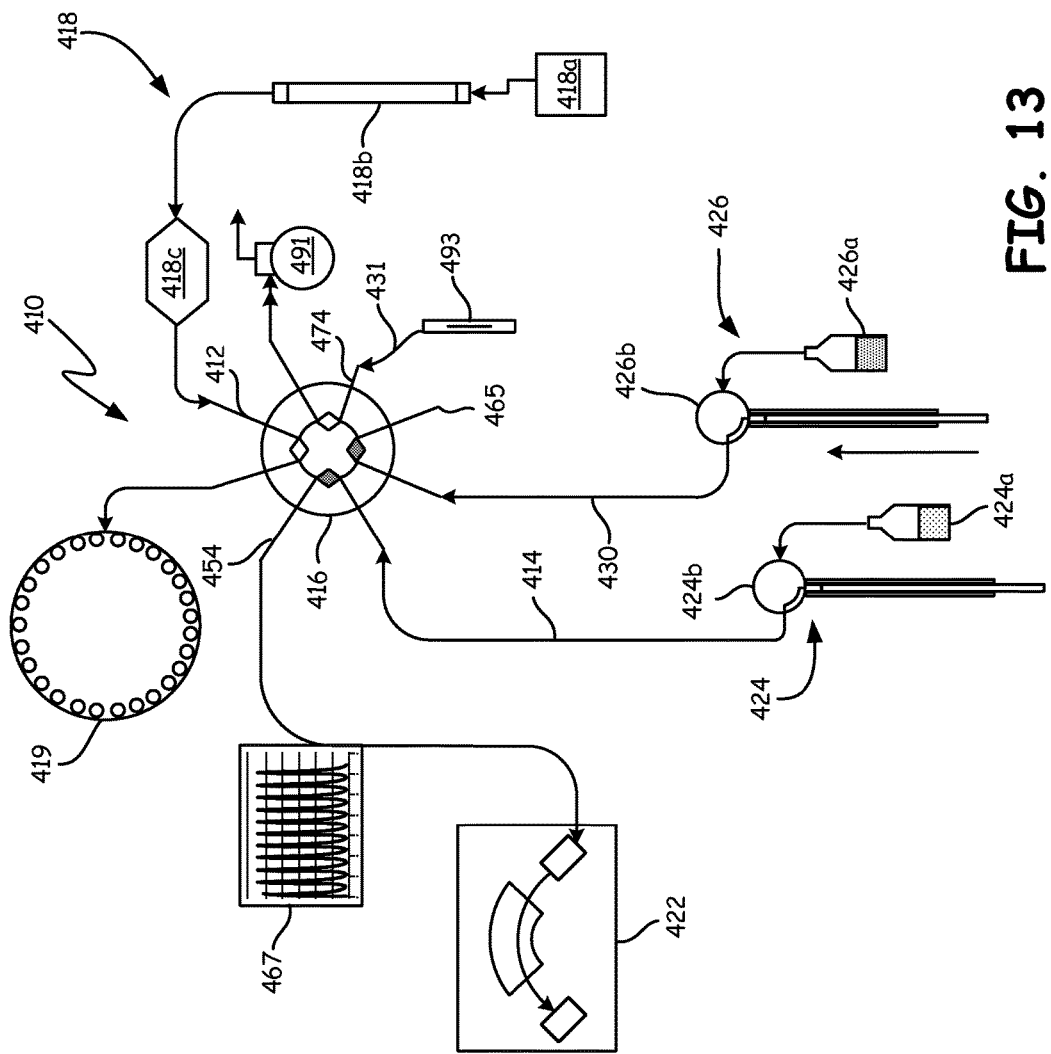
FIG. 13 is a schematic diagram of a two dimensional liquid analysis system employing a liquid sampling system of the present invention.

Another application of the present invention is illustrated in FIG. 13 for sampling the outlet of a high flow rate separation system, such as that known as "flash chromatography". Such a system may commonly be employed wherein a sample, such as a pharmaceutical, is purified, and the purified sample is collected. Liquid sampling system 410 includes a first dimension system 418 having a mobile phase supply 418a, a separation column 418b, and a detector 418c. Separation column 418b may be a flash column wherein milligram to gram quantities of compounds may be separated into individual components to be collected by fractionation using a fraction collection system depicted at 419. Primary stream 412 may be passed through liquid sampling valve 416, and further to fraction collector 419. In the instance wherein the primary stream flow rate is too large to flow through either detector 418c or liquid sampling valve 416 without causing excessive back pressure on separation column 418b, a stream splitter (not shown) may be installed upstream or downstream from detector 418c. Upon the expiration of a predetermined dwell period to fill shuttle 482 with a liquid aliquot sample at a first station in fluid communication with primary stream 412, a rotation of 90° of rotor 384 moves shuttle 482 to the second station, wherein second dimension carrier supply 424 motivates secondary stream 414 to flush the liquid aliquot sample from shuttle 482 into secondary path 454 along secondary stream 414 to second dimension analyzer 422, which may be a mass spectrometer. Motivation of secondary stream 414 may be derived from a pump 424b motivating second dimension carrier fluid from a reservoir 424a. Transfer of one liquid aliquot sample into secondary stream 414 represents one peak of the example sample trace illustrated at 467. A secondary bypass channel 498 may be configured in accordance with the flow rate of secondary stream 414 when a shuttle 482 is not in the second station in fluid communication with secondary path 454. In the event that second dimension analyzer 422 is a mass spectrometer, the flow rate of secondary stream 414 is preferably less than one milliliter per minute, and preferably as low as 100 microliter per minute. A secondary bypass channel 500 having a length and depth of approximately 125 microns may be desirable for such a flow rate. Rotation of rotor 434 to a third station brings shuttle 482 into fluid communication with discharge stream 430. As illustrated in FIG. 13, discharge stream 430 may be motivated by discharge supply 426, which may include a discharge fluid reservoir 426a motivated through liquid sampling valve 416 by a pump 426b. Flow of discharge stream 430 carries fluid from shuttle 482 in the third position along discharge path 474 to waste 465.

A further rotation of rotor 434 brings shuttle 482 into a fourth station in fluid communication with a sweep stream 431 along sweep path 474, and driven by a vacuum pump 491. A flow restrictor 493 may be employed to limit influx of sweep stream 431 along sweep path 474.

EXAMPLE

Figure 3:
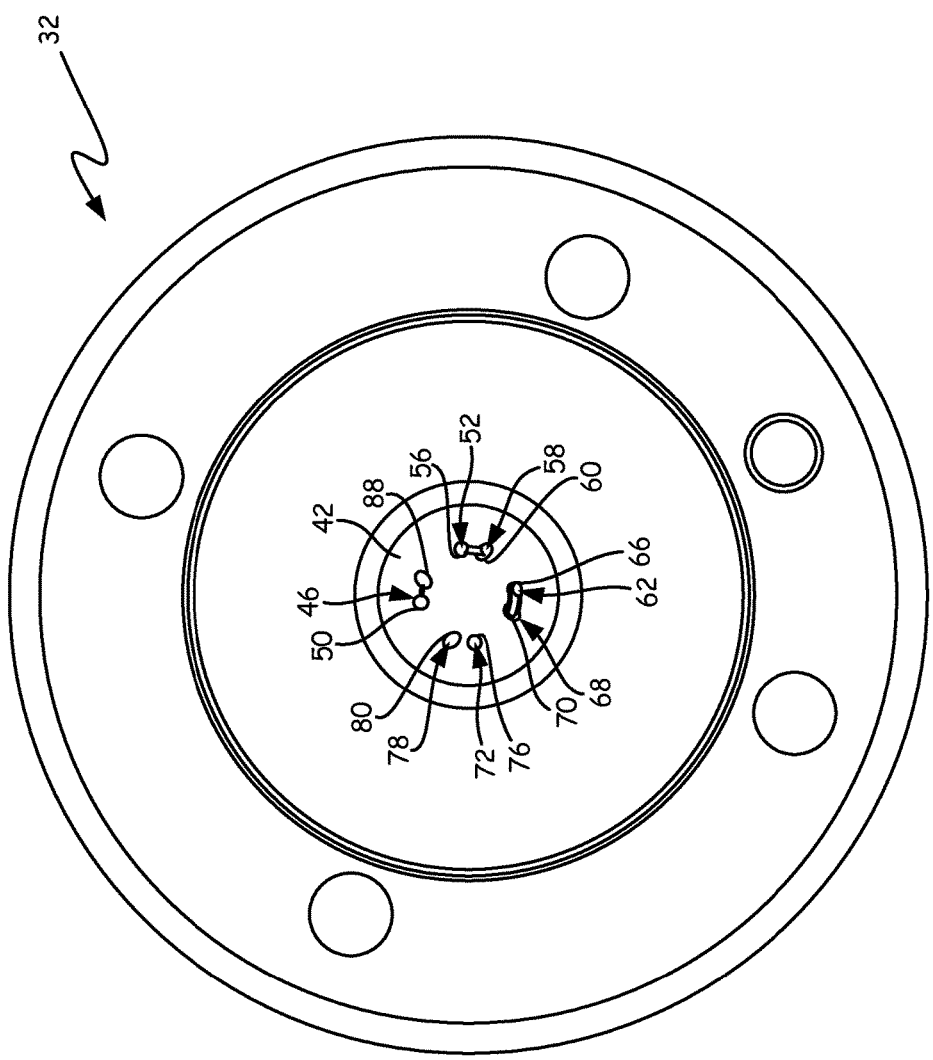
FIG. 3 is an end elevational view of a stator component of a liquid sampling valve of the present invention.
Figure 14:
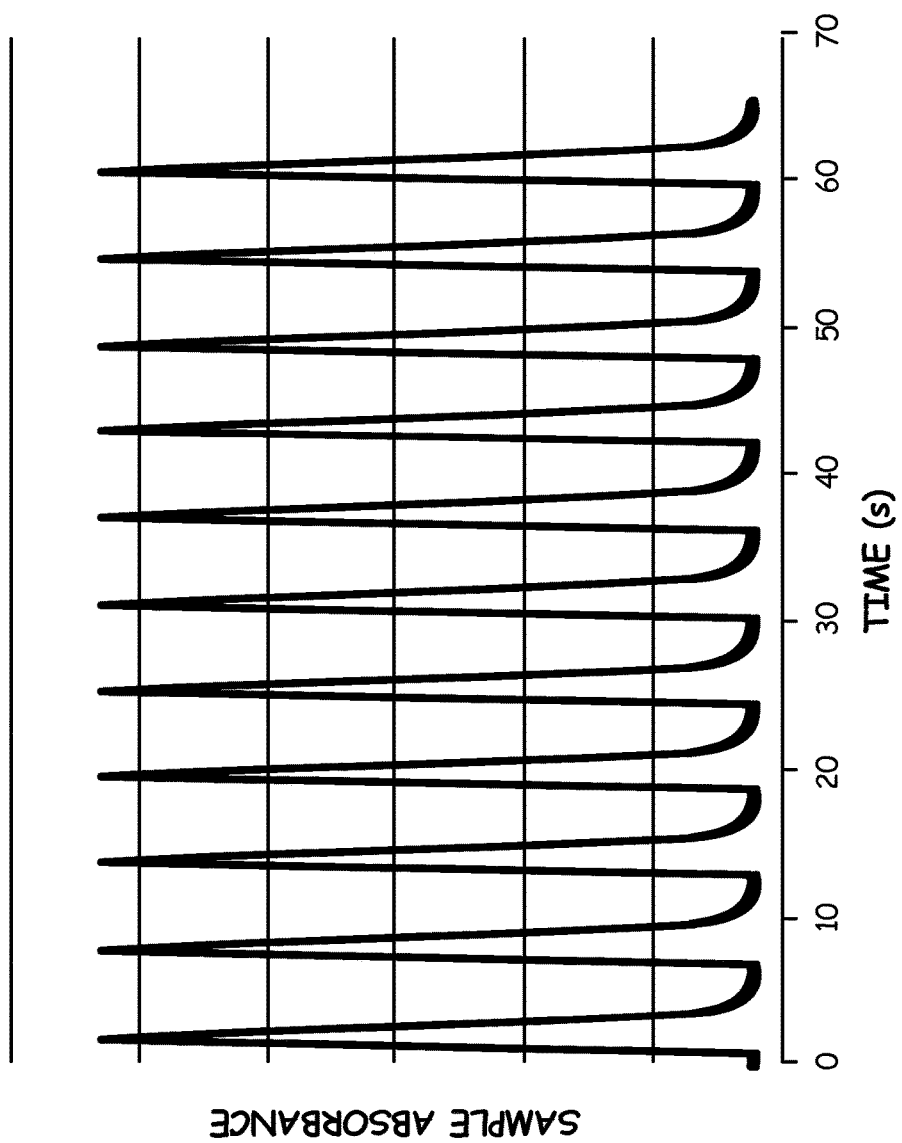
FIG. 14 is a representative ultraviolet detector trace analyzing transferred liquid samples in a secondary liquid stream carrier, wherein the samples are supplied to the secondary stream through a liquid sampling valve of the present invention.

An example liquid sampling valve was manufactured with a rotor machined with four equally circumaxially-spaced shuttles, each having a shuttle volume of 500 nanoliters. A stator in accordance with that illustrated in FIGS. 2-4 was secured to the rotor in a sealed, rotatable connection. An acetone primary stream was continuously flowed at a rate 500 microliters/minute thorough a primary stator passage set, thus filling each shuttle volume as it paused for a dwell period of 5,000 milliseconds at the first shuttle station. The sample volume of acetone contained in each shuttle was transferred to a second shuttle station in fluid communication with a secondary stator passage set. A secondary stream of methanol was passed through the secondary stator passage set at a continuous flow rate of 500 microliters/minute, such that the volume of acetone in the shuttle at the second station was transferred into an ultraviolet detector. The difference in absorbance between the flow of methanol and the absorbance of the 500 nanoliter aliquot samples of acetone are presented in FIG. 14 as peaks. The following Table 1 sets forth the conditions used in this example.

TABLE 1

| | | |
|---|---|---|
| Valve Transfer Period (90°) | 600 | Milliseconds |
| Valve Dwell Period | 5000 | Milliseconds |
| Fluid Transfer Flow Rate (methanol) | 500 | uL/min |
| Fluid Fill Flow rate | 500 | uL/min |
| Shuttle Volume | 500 | Nanoliters |
| Bypass Channel Dimension | 0.005 | Inches wide and deep |
| Detector Volume | 2.5 | uL |

The invention has been described herein in considerable detail in order to comply with the patent statutes, and to provide those skilled in the art with the information needed to apply the novel principles and to construct and use embodiments of the invention as required. However, it is to be understood that various modifications to the described embodiments may be accomplished without departing from the scope of the invention itself.

What is claimed is:

1. A liquid sample analysis system, comprising:
a first dimension liquid analysis apparatus for separating a first liquid into liquid analytes in a primary liquid stream;
a secondary liquid stream supply including second dimension pump for motivating a secondary liquid stream;
a liquid sampling valve for transferring a liquid sample from said primary liquid stream to said secondary liquid stream, said valve including a stator and a rotor that is rotatable with respect to said stator about a valve axis, said stator having a stator face and a plurality of passage sets each including at least two passages separately extending through said stator along a respective liquid path and opening to said stator face, first and second passages of a first passage set being fluidly connected in said stator, and third and fourth passages of a second passage set being fluidly connected in said stator, such that the primary liquid stream and the secondary liquid stream are continuously flowable through the stator, said rotor including a shuttle configured for receiving the liquid sample, wherein rotation of said rotor about said valve axis sequentially moves said shuttle into a plurality of circumaxially spaced stations; and
a second dimension liquid analysis apparatus for analyzing said liquid sample in said secondary liquid stream.

2. A liquid sample analysis system as in claim 1, including a first bypass groove extending between and fluidly connecting said first and second passages of said first passage set in said stator face.

3. A liquid sample analysis system as in claim 2, including a second bypass groove extending between and fluidly connecting said third and fourth passages of said second passage set in said stator face.

4. A liquid sample analysis system as in claim 1, including third and fourth passage sets each including at least two passages separately extending through said stator along a respective liquid path and opening to said stator face, fifth and sixth passages of said third passage set being fluidly connected in said stator, and seventh and eighth passages of said fourth passage set being fluidly connected in said stator.

5. A liquid sample analysis system as in claim 4 wherein a first station aligns said shuttle in fluid communication with said first and second passages at said stator face, a second station aligns said shuttle in fluid communication with said third and fourth passages at said stator face, a third station aligns said shuttle in fluid communication with said fifth and sixth passages at said stator face, and a fourth station aligns said shuttle in fluid communication with said seventh and eighth passages at said stator face.

6. A liquid sample analysis system as in claim 5 wherein said first passage includes a first opening at said stator face that is along a first circumference about said valve axis, and said second passage includes a second opening at said stator face that is along a second circumference about said valve axis, wherein said first circumference is radially displaced from said second circumference.

7. A liquid sample analysis system as in claim 6 wherein said third passage includes a third opening at said stator face that is along said first circumference, and said fourth passage includes a fourth opening at said stator face that is along said second circumference about said valve axis.

8. A method for transferring a liquid sample from a primary liquid stream to a secondary liquid stream for analysis of the liquid sample in the secondary liquid stream, said method comprising:
(a) providing a liquid sampling valve having:
(i) a stator with a stator face and a plurality of passage sets each including at least two passages separately extending through said stator along a respective liquid path and opening to said stator face, a first passage set having first and second passages, a second passage set having third and fourth passages, and a third passage set having fifth and sixth passages, such that the primary liquid stream and the secondary liquid stream are continuously flowable through the stator;
(ii) a rotor having a rotor face in fluid-tight contact with said stator face, said rotor face including a shuttle;
(b) pumping the primary liquid stream along a primary liquid path through said first passage to fill said shuttle with the liquid sample while said shuttle is positioned at a first station;
(c) rotating said rotor in a first circumaxial direction about a valve axis to position said shuttle at a second station in fluid communication with said second passage set;
(d) pumping the secondary liquid stream along a secondary liquid path through said third passage to transfer the liquid sample from said shuttle to the secondary liquid stream and out through said fourth passage;
(e) further rotating said rotor in said first circumaxial direction about said valve axis to position said shuttle at a third station in fluid communication with said third passage set; and
(f) pumping a discharge fluid along a discharge path through said fifth passage to transport the secondary liquid out from said shuttle through said sixth passage.

9. A method as in claim 8 wherein said stator includes a seventh passage extending through said stator and opening to said stator face, said seventh passage not fluidly connectable to said first, second, or third passage sets.

10. A method as in claim 9, including further rotating said rotor in said first circumaxial direction about said valve axis to position said shuttle at a fourth station in fluid communication with said seventh passage.

11. A method as in claim 10, including withdrawing the discharge fluid from said shuttle through said seventh passage.

12. A method as in claim 11, including providing a vacuum pump fluidly coupled to said seventh passage to evacuate said shuttle when positioned at said fourth station.

13. A method as in claim 11, including further rotating said rotor in said first circumaxial direction about said valve axis to position said shuttle at said first station in fluid communication with said first passage set.

14. A method as in claim 8 wherein said rotor discontinuously rotates about said valve axis by temporarily stopping at each of said first, second, and third stations.

15. A method as in claim 14 wherein said rotor temporarily stops at said fourth station.

16. A method as in claim 8 wherein said stator includes a first bypass groove extending between and fluidly connecting said first and second passages of said first passage set in said stator face, and a second bypass groove extending between and fluidly connecting said third and fourth passages of said second passage set in said stator face.

17. A method as in claim 16, including continuously pumping the primary liquid stream along said first bypass groove and out through said second passage, including when said shuttle is not positioned at said first station.

18. A method as in claim 17, including continuously pumping the secondary stream along said second bypass groove and out through said fourth passage, including when said shuttle is not positioned at said second station.

19. A method for transferring a liquid sample from a primary liquid stream to a secondary liquid stream for analysis of the liquid sample in the secondary liquid stream, said method comprising:

(a) providing a liquid sampling valve having:
  (i) a stator with a stator face, a primary stator passage extending along a primary path through said stator and opening to said stator face, an inlet secondary stator passage extending along a secondary path through said stator and opening to said stator face, an outlet secondary stator passage extending along the secondary path through said stator and opening to said stator face, said inlet and outlet secondary stator passages being fluidly connected in said stator by a secondary bypass channel, an inlet discharge passage extending along a discharge path through said stator and opening to said stator face, and an outlet discharge passage extending along the discharge path through said stator and opening to said stator face; and
  (ii) a rotor having a rotor face in fluid-tight contact with said stator face at an interface, said rotor face including a shuttle;
(b) delivering the primary liquid stream along the primary path through said primary stator passage to fill said shuttle with the liquid sample;
(c) rotating said rotor in a first circumaxial direction about an axis of rotation to bring said shuttle into fluid communication with said inlet and outlet secondary stator passages, and out of fluid communication with said primary stator passage;
(d) delivering the secondary liquid stream along the secondary path to transport the liquid sample with the secondary liquid stream out from said shuttle through said outlet secondary passage;
(e) further rotating said rotor in said first circumaxial direction about said axis of rotation to bring said shuttle into fluid communication with said inlet and outlet discharge passages, and out of fluid communication with said inlet and outlet secondary stator passages;
(f) performing a discharge operation along said discharge path to transport the secondary liquid out from said shuttle through said outlet discharge passage; and
(g) further rotating said rotor in said first circumaxial direction about said axis of rotation to bring said shuttle into fluid communication with said primary stator passage.

* * * * *